(12) United States Patent
Gupta

(10) Patent No.: US 7,615,546 B2
(45) Date of Patent: Nov. 10, 2009

(54) TOPICAL DELIVERY SYSTEM FOR PHYTOSTEROLS

(75) Inventor: Shyam K Gupta, Scottsdale, AZ (US)

(73) Assignee: BioDerm Research, Scottsdale, AZ (US)

( * ) Notice: Subject to any disclaimer, the term of this patent is extended or adjusted under 35 U.S.C. 154(b) by 0 days.

(21) Appl. No.: 12/210,266

(22) Filed: Sep. 15, 2008

(65) Prior Publication Data

US 2009/0042846 A1 Feb. 12, 2009

Related U.S. Application Data

(63) Continuation-in-part of application No. 11/161,856, filed on Aug. 19, 2005, now abandoned, and a continuation-in-part of application No. 12/139,659, filed on Jun. 16, 2008.

(51) Int. Cl.
| | |
|---|---|
| *A61K 31/58* | (2006.01) |
| *A61K 31/575* | (2006.01) |
| *A61K 31/23* | (2006.01) |
| *A61K 31/22* | (2006.01) |
| *C07J 53/00* | (2006.01) |
| *C07J 9/00* | (2006.01) |
| *C07C 69/017* | (2006.01) |

(52) U.S. Cl. .................. 514/172; 514/173; 514/546; 514/552; 552/510; 552/514; 552/544; 552/547; 560/129

(58) Field of Classification Search .................. None
See application file for complete search history.

(56) References Cited

U.S. PATENT DOCUMENTS 5,733,572 A * 3/1998 Unger et al. ................ 424/450

6,407,085 B1 * 6/2002 Kief ........................... 514/182

* cited by examiner

*Primary Examiner*—Shaojia Anna Jiang
*Assistant Examiner*—Eric S Olson

(57) ABSTRACT

This invention relates to certain sugar esters of phytosterols of formula (I). These esters are useful for topical application, and for the treatment of skin condition, including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof;

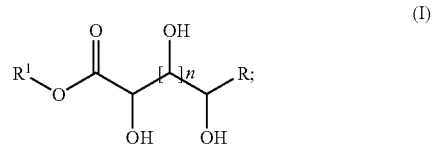

(I)

Wherein,
n=0, 1, 2, or 3; and
R=H, —CH$_2$OH, —CH(OH)—CH$_2$OH, —CH(OH)—CH(OH)—CH$_2$OH; and
R$^1$=Substituent selected from a sapogenin, steroid, or terpenoid.

17 Claims, 9 Drawing Sheets

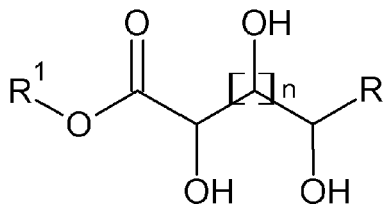
Sugar Ester of a Polycyclic Polyisoprenoid
Wherein,
n = 0, 1, 2, or 3; and
R = H, -CH$_2$OH, -CH(OH)-CH$_2$OH, -CH(OH)-CH(OH)-CH$_2$OH; and
R$^1$ = Substituent selected from a sapogenin, steroid, or triterpenoid
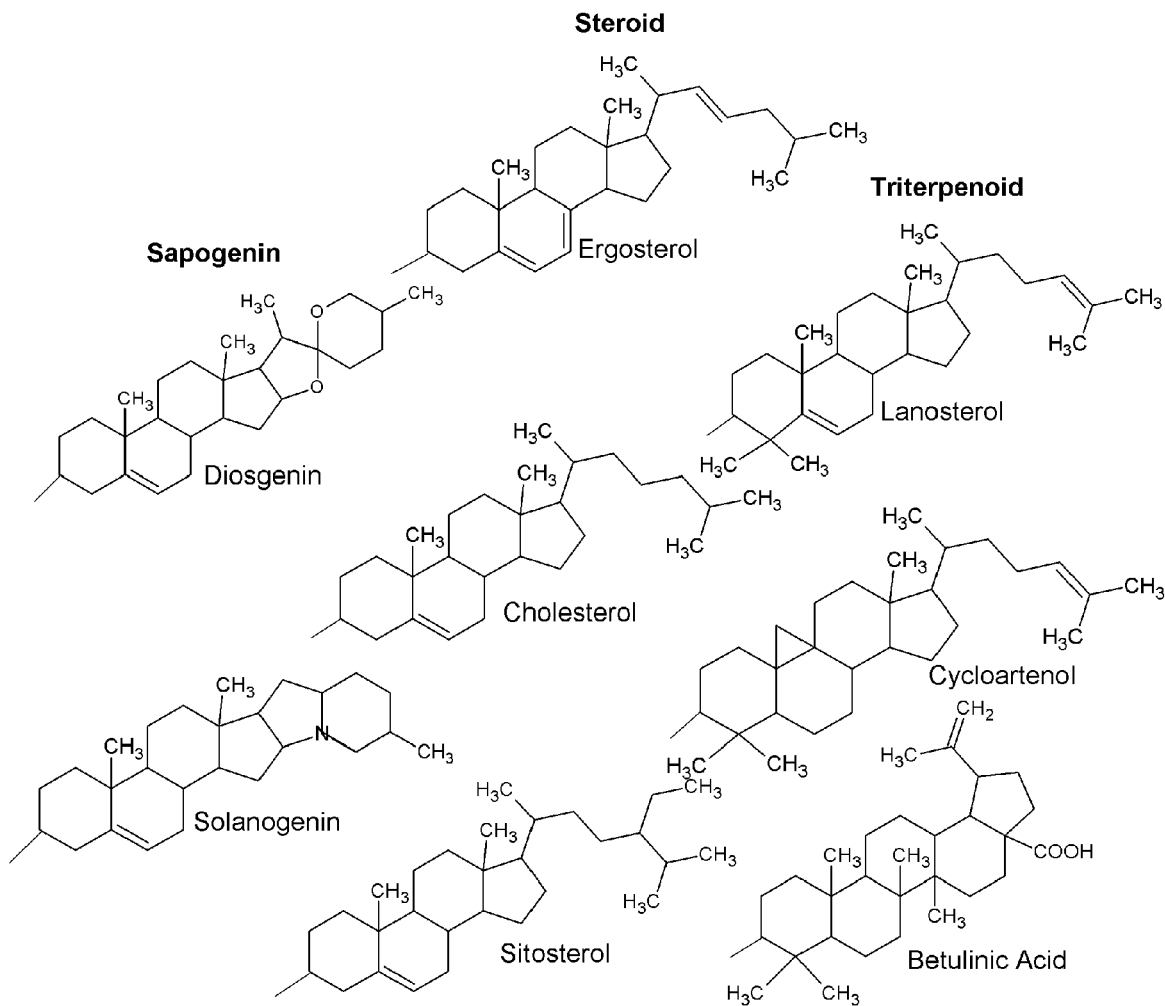
Fig. 1. Sugar Esters of Polycyclic Polyisoprenoids

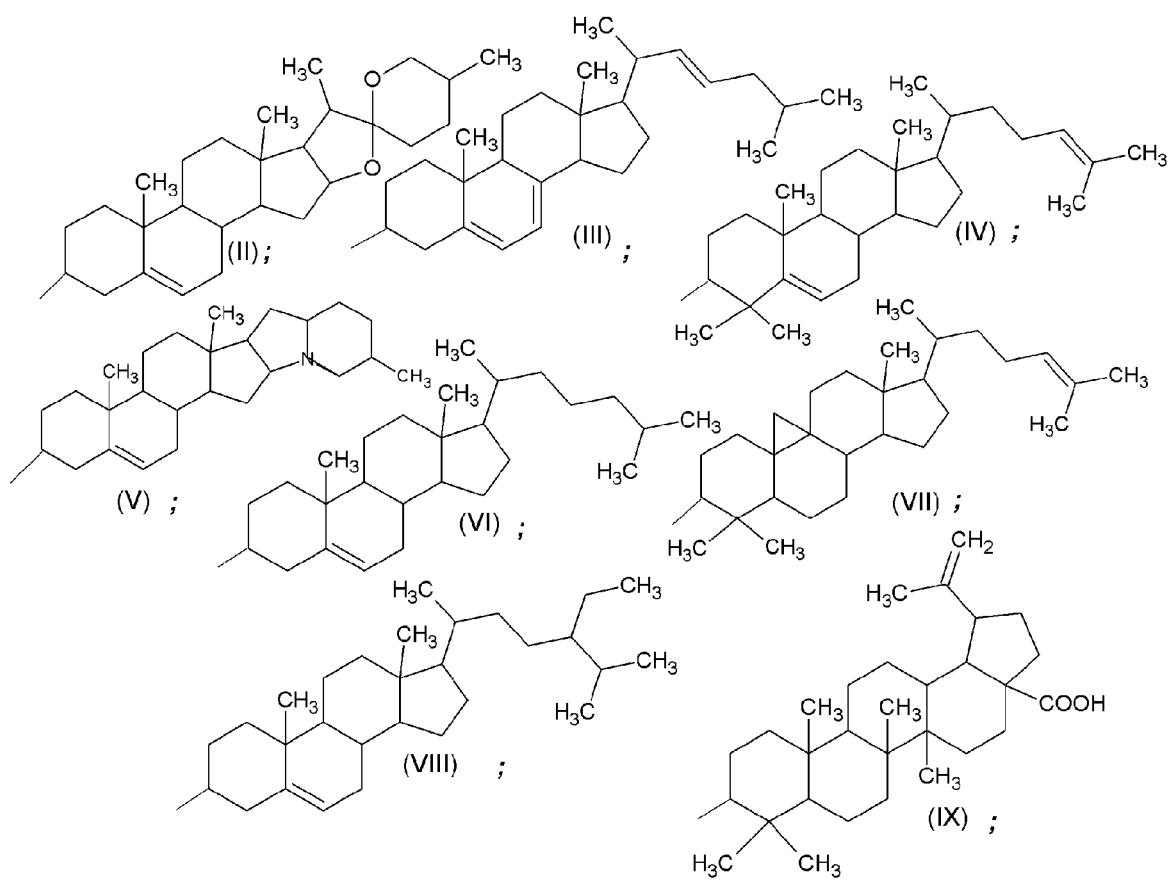
Fig. 2. Polycyclic Polyisoprenoid Substituents in Fig 1.

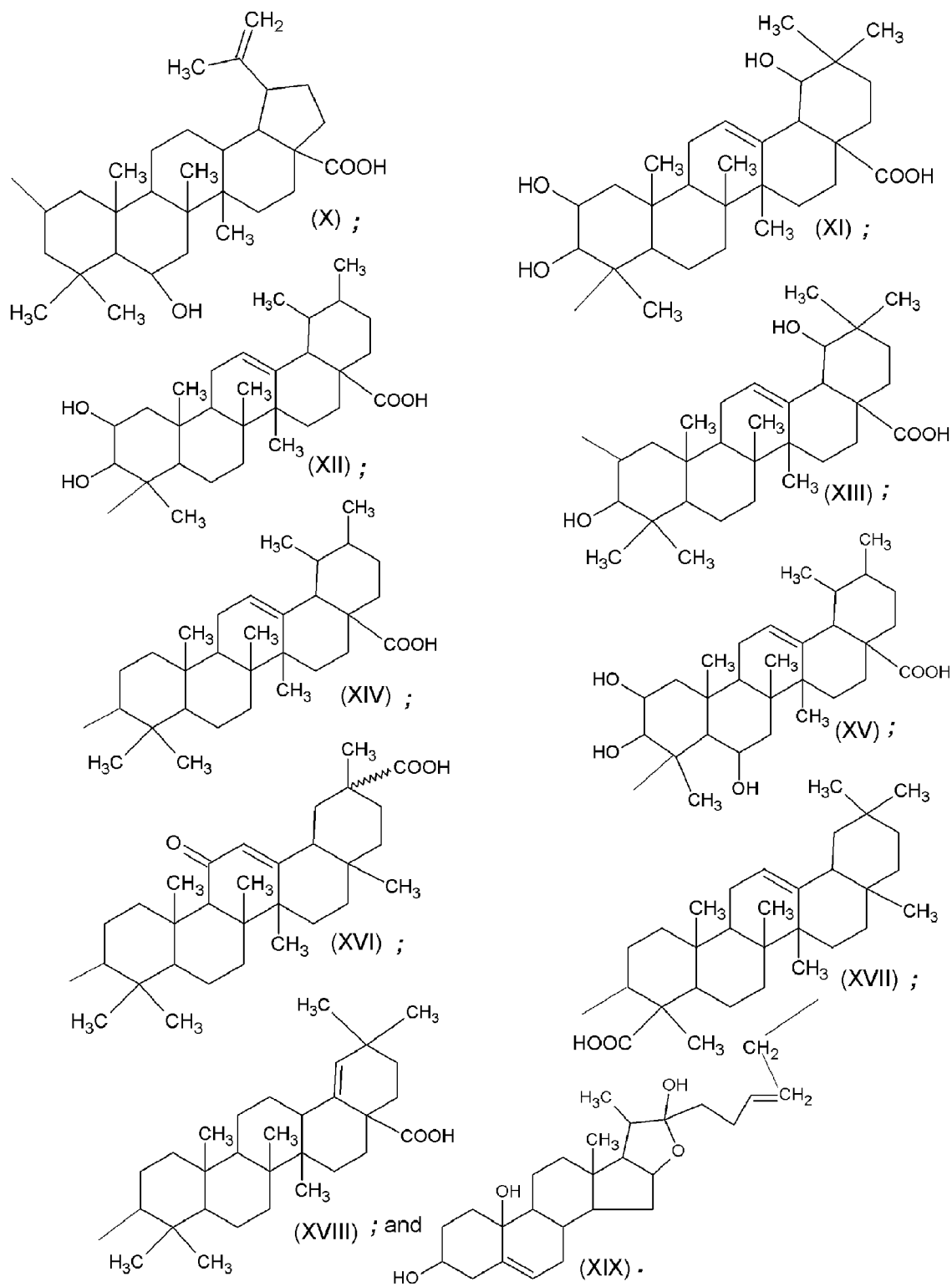
Fig. 3. Additional Polycyclic Polyisoprenoid Substituents in Fig 1.

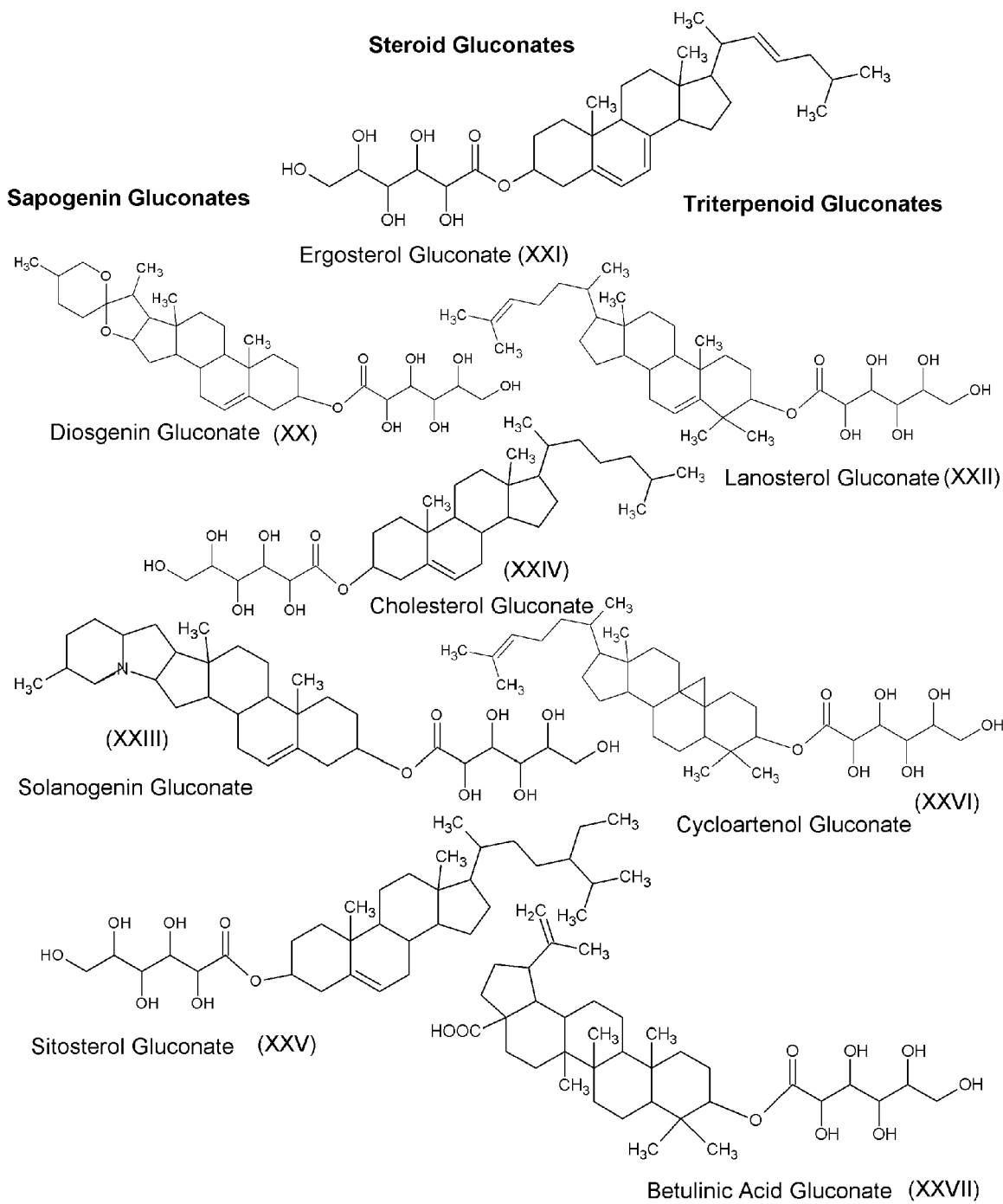
Fig. 4. Gluconate Esters of Sapogenins, Steroids, and Triterpenoids

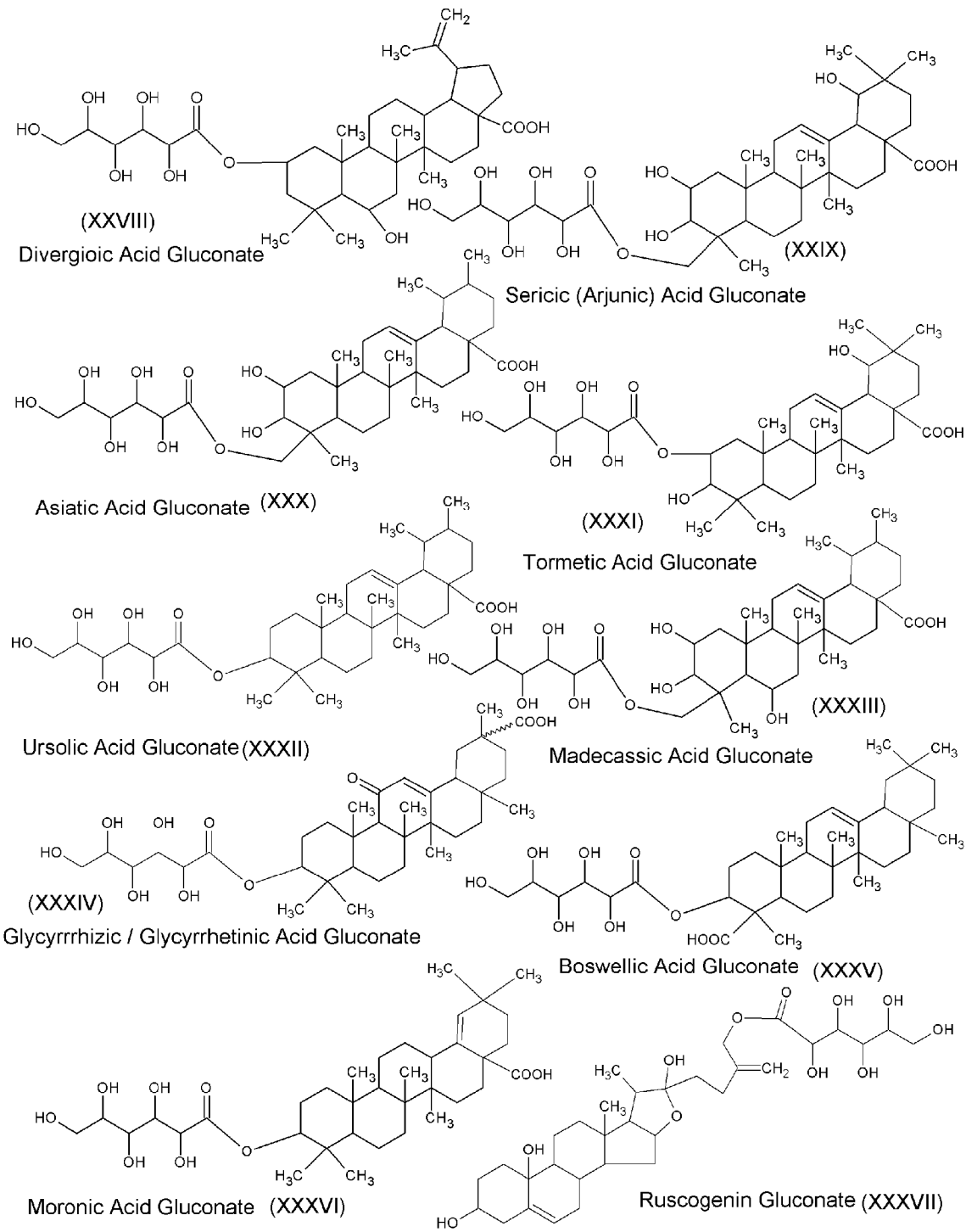
Fig. 5. Gluconate Esters of Polycyclic Triterpenoids

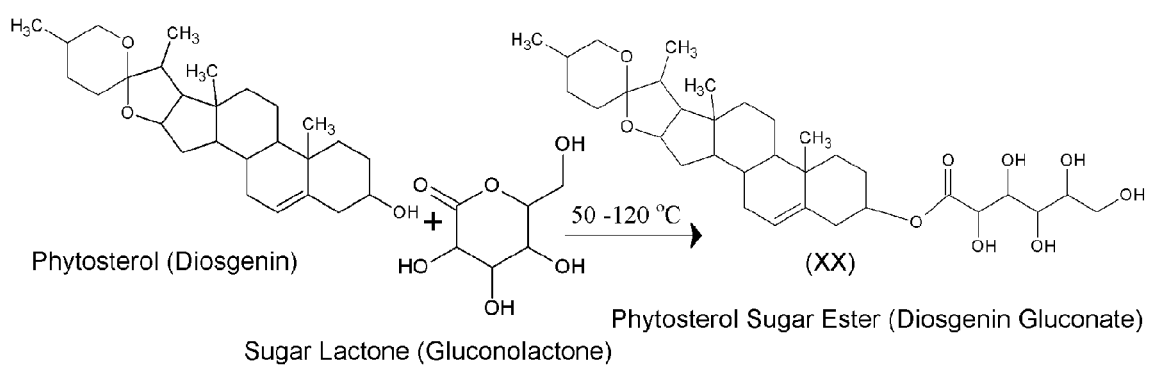
Fig. 6. Process of Phytosterol Sugar Esters from A Phytosterol (Diosgenin) & A Natural Sugar Lactone (Gluconolactone)

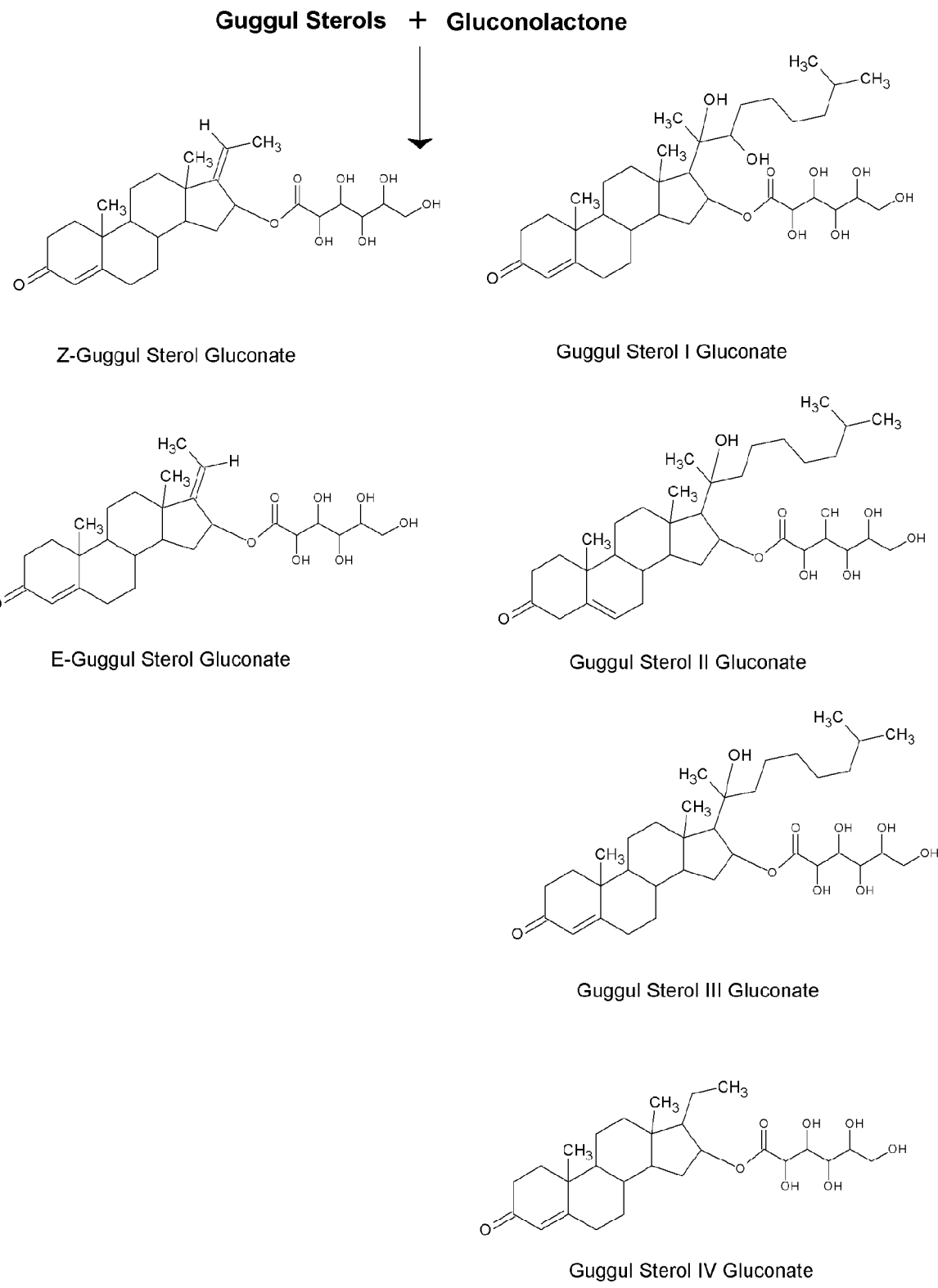
Fig. 7. Guggul Sterols Gluconates & Isomers

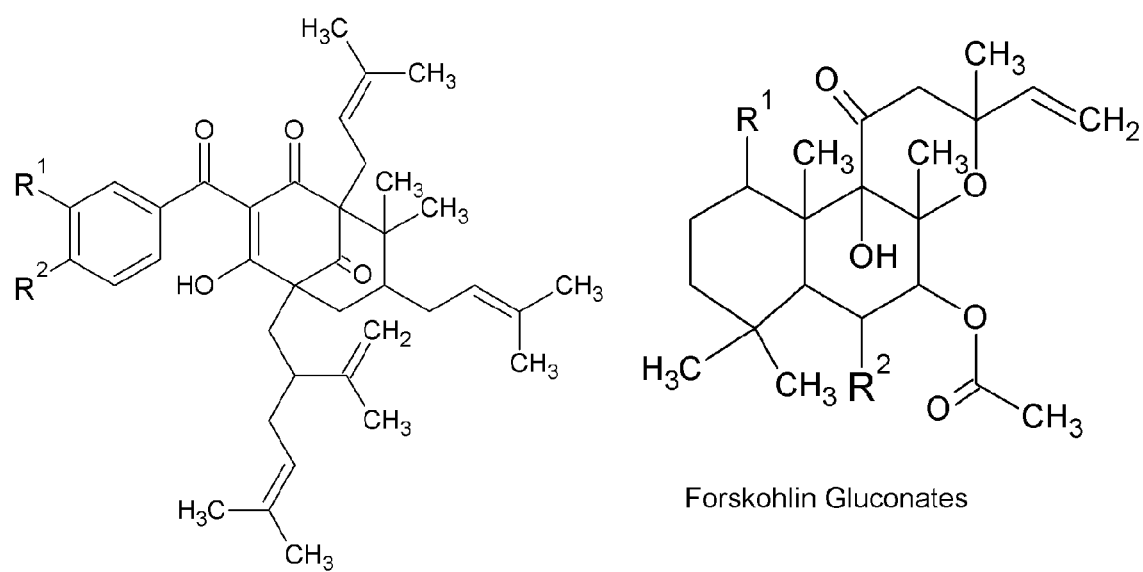
Garcinol Gluconates
Forskohlin Gluconates
R¹, R² = OH; and/or
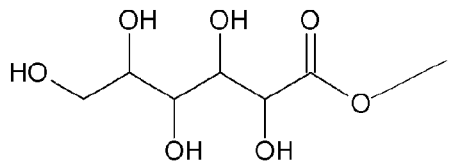
Fig. 8 Polyisoprenoid Gluconates

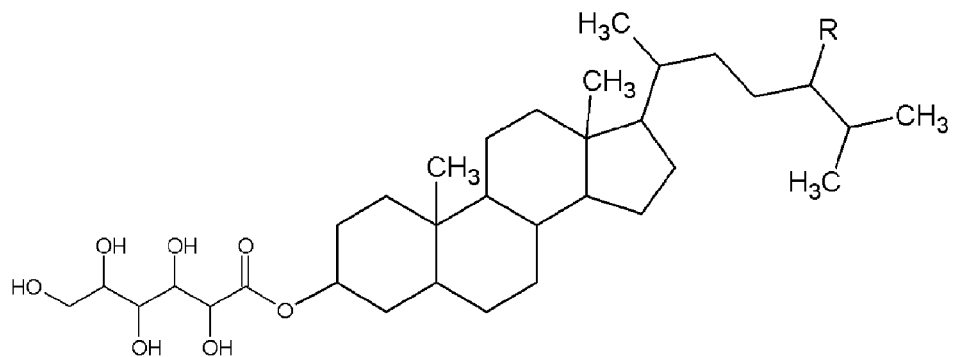
Campesterol Gluconate : R = $CH_3$, $\Delta^5$
Campestanol : R = $CH_3$
Sitosterol : R = $-CH_2CH_3$, $\Delta^5$
Stigmastanol : R = $-CH_2CH_3$
Stigmasterol : R = $-CH_2CH_3$, $\Delta^{5, 22}$
Fig. 9. Tall Oil (Pine) Sterols Gluconates

TOPICAL DELIVERY SYSTEM FOR PHYTOSTEROLS

The present invention is a continuation-in-part of U.S. patent application Ser. No. 11/161,856 (filed on 19 Aug. 2005) now abandoned, and continuation-in-part of U.S. patent application Ser. No. 12/139,659 (filed on 16 Jun. 2008).

BACKGROUND OF THE INVENTION

Phytosterols are a class of polycyclic polyisoprenoids compounds biogenetically derived from isoprene units. For practical purpose, the term "phytosterol" and "polycyclic polyisoprenoid" are used interchangeably in the present invention. The most important of these—sterols, sapogenins, phytosterols, and terpenoids—have structures similar to plant and animal steroids, which have a basic structure of three linked six-membered rings and one five-membered ring. Steroids and terpenoids with hydroxyl groups have names that end in "ol," such as cholesterol and menthol, respectively. A number of these are known to have medicinal properties (Singh et al., Current Science, Vol. 89, No. 2, 269-290 (2005)). Most of these polycyclic polyisoprenoids are known to be water insoluble, which results in their poor bioavailability from any topical compositions.

The present invention relates to sugar esters of said phytosterols, which are conjugates of phytosterols with certain sugar lactones; in their optically active, inactive, or racemic forms (such as d, l, dl, and meso); wherein phytosterol moiety provides the alcohol part, and the sugar lactone moiety provides the carbonyl part of said sugar esters. These esters are useful for the treatment of multiple skin conditions and ailments, including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

The sugar esters of the present invention are prepared by a novel method, wherein said phytosterols undergo a chemical reaction with certain sugar lactones to form said esters.

This invention also relates to a method of treatment of skin condition and ailment including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

DESCRIPTION OF THE RELATED ART

The polycyclic polyisoprenoids are a class of polycyclic compounds biogenetically derived from isoprene units. The most important of these—sterols, sapogenins, terpenoids, and phytosterols—have structures similar to plant and animal steroids. Most of these are obtained from natural source, for example, Wong et al. (Journal of Wood Science, Vol. 47, 400 (2001); Foster et al., TAPPI, Vol. 63, No. 12, 103 (1980); and Robinson et al. (U.S. Pat. No. 6,057,462).

Steroids are waxy, soapy or greasy in texture, thus are more soluble in oil than water. The best-known animal sterol is cholesterol, which, despite its negative connotation, is essential for life and a critical component of cell membranes, organs, the brain and the nervous system. Just as cholesterol is the human precursor to all steroid hormones, such as cortisol, estrogen, progesterone, and testosterone, beta-sitosterol is the plant's precursor to growth and reproductive hormones.

Sapogenins that are stored in plants with sugars attached are called saponins. Some sapogenins, the non-sugar portion of a saponin, can mimic or regulate steroid hormones or hormone precursors. Yams (*Dioscorea* spp.), which contain variable amounts of the sapogenin diosgenin, can be converted into corticosteroids, dehydroepiandrosterone (DHEA), estrogen and progesterone in the laboratory, whereas the body cannot convert diosgenin into steroid hormones. Diosgenin has a weak estrogenic or progesteronic effect, which may account for its historical folk use by women.

The yam North American herbalists use most often is *D. villosa*, which isn't as rich in diosgenin as are other species. Yam species used for food are lower in sapogenins than their wild progenitors (saponins are distasteful and can be toxic). Sapon, which means soap, refers to the saponins' tendency to foam in water.

Fenugreek (*Trigonella foenum-graecum*) is richer in diosgenin and other saponins than yams. Traditionally, fenugreek was prescribed to increase breast milk production and breast size. Although few studies support these indications, fenugreek saponins can lower cholesterol and blood lipids.

The most celebrated saponins are ginsenosides from Korean ginseng (*Panax ginseng*). Although ginseng has been promoted as an aphrodisiac, ginsenosides resemble adrenal hormones more than sex hormones. Ginsenosides mildly stimulate the adrenal and pituitary glands, among other actions, which may account for ginseng's anti-fatigue and adaptogenic effects. Another saponin-rich herb used throughout the Americas is sarsaparilla (*Smilax officinalis*), traditionally used to increase libido and flavor root beer.

Phytosterols can mimic or regulate human hormones or hormone precursors. They are thought to be the essential components of bee pollen, pumpkin seeds, pygeum (*Pygeum africanum*) and saw palmetto (*Serenoa repens, S. serulatta*)—all of which are used to treat enlarged prostates and prostatitis. Phytosterol steroid mimicry also contributes to the anti-inflammatory effect of cold-pressed flaxseed and olive oils.

Anthropologists and medical doctors who have studied the East African Masai tribe have shown that although 66 percent of their daily caloric intake comes from animal fat—meat, milk and yogurt—their serum cholesterol levels are low and cardiovascular disease is virtually nonexistent. Masai's minor but judicious use of wild plant foods keeps their systems balanced. They seem to add enough wild plants to milkand meat-based soups to make them bitter and also drink herbal teas with meals, regularly chew tree barks and gums, use medicinal plants, and add herbs to their home-brewed honey beer. It is reported that 9 of 12 common Masai plant-derived food additives contain cholesterol-lowering phytosterols, saponins and/or phenolics.

Nuts are the richest source of phytosterols in Western diets, and numerous epidemiological studies show that diets rich in whole nuts are associated with a decreased incidence of cardiovascular disease. In numerous clinical studies, subjects who ate 40 to 100 g/day of almonds, hazelnuts, macadamia nuts, pecans, pistachios and walnuts—nuts that often replaced 20 to 30 percent of their daily calories—experienced lowered serum triglycerides, total cholesterol and LDL cholesterol.

Phytosterols are poorly absorbed and lower cholesterol by interfering with its absorption in the small intestine.

Cold-pressed unrefined vegetable oils such as flaxseed, hazelnut, olive, sesame, wheat germ and walnut are excellent sources of phytosterols, which also contribute greatly to the unique tastes, textures and aromas of these oils. Refining oil removes 20 to 60 percent of phytosterols, and hydrogenation removes an additional 20 to 40 percent.

Algae and fungi also manufacture phytosterols. For example, ergosterol and other sterols from red yeast grown on rice have been shown to lower cholesterol. Asians using red rice yeast for health typically consume 14 to 55 g/day. Anecdotal reports that mushrooms, seaweed, and spirulina lower cholesterol could be attributed to the fucosterol, sitosterol, ergosterol, and other sterols they contain.

Relative to relevant prior art, the following are worthy of note. U.S. Pat. Nos. 4,602,003 and 4,461,762 (Malinow) disclose synthetic sapogenin and sterol compounds, administered orally to warm-blooded animals that inhibit the absorption of cholesterol, and are useful in the treatment of hypercholesterolemia. Particular compounds suitable for such purposes include glycosides with spirostane, spirostene, or cholesterol aglycones, and esters of spirostanes, spirostenes and cholesterol. None of these are sugar esters related to the present invention. According to Malinow, certain water/alcohol soluble extracts from plant sources have been found to reduce cholesterolemia in chicks, pigs and rats (P. Griminger, et al., "Dietary Saponin and Plasma Cholesterol in the Chick." Proc. Soc. Exp. Biol. Med. 99:424-426, 1958; H. A. I. Newman, et al. "Dietary Saponins, a Factor Which May Reduce Liver and Serum Cholesterol Levels." Poultry Sci. 37:42-46, 1958; B. Morgan, et al., "The Interactions Between Dietary Saponin, Cholesterol and Related Sterols in the Chick." Poultry Sci. 51:677-682, 1972; D. L. Topping, et al, "Effects of Dietary Saponins in Fecal Bile Acids and Neutral Sterols, Plasma Lipids, and Lipoprotein Turnover in the Pig." Am. J. Clin. Nutr. 33:783-786, 1980; D. G. Oakenfull, et al., "Effects of Saponins on Bile-acids and Plasma Lipids in the Rat." Br. J. Nutr. 42:209-216, 1979; and D. L. Topping, et al., "Prevention of Dietary Hypercholesterolemia in the Rat by Soy Flour High and Low in Saponins", Nutr. Rep. Int. 22:513-519, 1980). More specifically, extracts from alfalfa hay are known to be active in reducing the absorption of dietary cholesterol. Although such alfalfa extracts are of unknown composition, they are found to contain saponins identifiable by thin-layer chromatography. The alfalfa extracts contain, in addition to saponins, unspecified amounts of carbohydrates, amino acids, peptides, pigments, and free aglycones removed from alfalfa hay by the water-alcohol solvent used during their preparation. Such crude extracts are sometimes referred to herein as "alfalfa saponins" as an operational definition. These alfalfa extracts reduce the intestinal absorption of cholesterol in rats and monkeys (M. R. Malinow, et al., "Cholesterol and Bile Acid Balance in *Macaca fascicularis*: Effects of Alfalfa Saponins." J. Clin. Invest. 67:156-162, 1981). The capacity of such alfalfa extracts to interfere with cholesterol absorption is enhanced by partial acid hydrolysis as reported in M. R. Malinow, et al., "Effect of Alfalfa Saponins on Intestinal Cholesterol Absorption in Rats." Am. J. Clin. Nutr. 30:2061-2067, 1977; and U.S. Pat. No. 4,242,502 (Malinow, et al.)). Digitonin binds cholesterol in vitro, inhibits the intestinal absorption of cholesterol, and prevents the hypercholesterolemia expected in monkeys ingesting high-fat, high cholesterol foods (M. R. Malinow, et al, "Prevention of Hypercholesterolemia in Monkeys (*Macaca fascicularis*) by Digitonin, Am. J. Clin. Nutr., 31:814-818, 1978). But, digitonin is costly. Diosgenin has also been reported to inhibit the absorption of cholesterol in rats when given in a massive dose (1000 mg/kg) (M. N. Cayen, et al., "Effect of Diosgenin on Lipid Metabolism in Rats", J. Lipid Res. 20: 162-174, 1979). It has been reported that toxicity of plant saponins is decreased in rats, mice, and birds by cholesterol in the diet (J. O. Anderson, "Effect of Alfalfa Saponin on the Performance of Chicks and Laying Hens." Poult. Sci. 36:873-876, 1957; I. Ishaaya, et al., "Soyabean Saponins. IX. Studies of Their Effects on Birds, Mammals and Cold-blooded Organisms." J. Sci. Food Agric., 20:433-436, 1969; G. Reshef, et al., "Effect of Alfalfa Saponins on the Growth and Some Aspects of Lipid Metabolism of Mice and Quails." J. Sci. Food Agric. 27:63-72, 1976; E. B. Wilcox, et al., "Serum and Liver Cholesterol, Total Lipids and Lipid Phosphorus Levels of Rats Under Various Dietary Regimes." Am. J. Clin. Nutr., 9:236-243, 1961). Despite these encouraging results, it has remained a problem that plant extracts, which are of variable composition, contain a volume of non-useful chemical substances. It is difficult, due to the variations in composition, to set a standard dosage or predict the impurities present. Thus, such extracts are not well suited for use by humans. Furthermore, purification of plant extract substances and synthesis of saponins suspected to exist in plants are likely to be very costly due to the anticipated complexity of the required procedures. Malinow disclosed that certain synthetically produced, pure "sapogenin-derived" compounds, e.g., substances compounded from spirostane, spirostene, or sterol-derived" compounds are non-toxic. Such compounds depress cholesterol absorption more effectively than alfalfa extracts on a weight basis and thus can be administered in reasonably sized doses. Because the chemical compositions of these substances are known and because they can be synthesized at a high degree of purity, they are suitable for use by any warm-blooded animal, including humans. Precursor substances for use in the synthesis are available as by-products of present industrial processes. For example, one spirostane compound (tigogenin) is currently a wasted by-product of digitalis manufacture.

Unless administered in massive amounts, pure sapogenins do not significantly bind cholesterol or inhibit its absorption. It is only when compounded with another moiety that sapogenins have the desired effect. Examples of such sapogenin compounds are compounds of tigogenin and diosgenin, particularly glycosides having tigogenin or diosgenin as an aglycone. Although it is not established that the size of the non-sapogenin moiety has any effect on a compound's ability to inhibit cholesterol absorption, at least one glycoside with a relatively longer sugar moiety has an increased biological activity in regard to cholesterol absorption. Specifically, cellobiose-sapogenins are more active than glucose-sapogenins having the same aglycone. Of such substances, cellobiose-tigogenin is particularly active to inhibit cholesterol absorption. Somewhat less active is cellobiose-diosgenin, perhaps due to the presence of a double bond in the spirostene aglycone of diosgenin.

The above problem is further illustrated in U.S. Pat. No. 7,354,956 (Besne), which relates to a composition containing a sapogenin, and/or a sapogenin ester, and to the use of a sapogenin and/or a sapogenin ester to manufacture a composition that is suitable for topical application to the skin, and in a method wherein sapogenin and/or a sapogenin ester are used as agents for the of smoothing out wrinkles and fine lines, in particular expression wrinkles and fine lines. The sapogenin may be used/provided in the form of a natural extract containing it. A preferred sapogenin is diosgenin.

Murray et al. (CA 2563830) disclose certain esters of steroids that are suitable for topical administration.

Clarkson (GB 1183504) discloses certain esters of steroid carboxylic acid for pharmaceutical application.

Lee et al. (U.S. Pat. No. 7,282,521) disclose certain moronic acid derivatives, which have antiviral activity, along with compositions containing the same and methods of use thereof.

Irrespective of prior art methods mentioned above, no suitable solution for the topical delivery of polycyclic polyisoprenoids, such as sapogenins, steroids, and triterpenoids, has been disclosed. The present invention circumvents that difficulty.

BRIEF DESCRIPTION OF THE SEVERAL VIEWS OF THE DRAWINGS

FIG. 1 Sugar Esters of Polycyclic Polyisoprenoids.
FIG. 2 Polycyclic Polyisoprenoid Substituents in FIG. 1.
FIG. 3 Additional Polycyclic Polyisoprenoid Substituents in FIG. 1.
FIG. 4 Gluconate Esters of Sapogenins, Steroids, and Triterpenoids.
FIG. 5 Gluconate Esters of Polycyclic Triterpenoids.
FIG. 6 Process of Phytosterol Sugar Esters from a Phytosterol (Diosgenin) and a Natural Sugar Lactone (Gluconolactone).
FIG. 7 Guggul Sterol Gluconates and Isomers.
FIG. 8 Polyisoprenoid Gluconates.
FIG. 9 Tall Oil (Pine) Gluconates.

DETAILED DESCRIPTION

The oil on the surface of skin is a complex mixture of sebum, lipids (from the surface skin cells), sweat and environmental material. Sebum is produced by sebaceous glands. These are found over most of the body, although there are few on the hands or feet and none on the palms and soles. Sebaceous glands on the mid-back, forehead and chin are larger and more numerous than elsewhere (up to 400-900 glands per square centimeter). They are also numerous in the ear canal and around the genitals. The sebaceous gland consists of lobes connected by ducts, which are lined with cells similar to those on the skin surface. The sebum flow dynamics at the skin surface results from a multi-step process starting with sebocyte proliferation, intracellular lipid synthesis, cell lysis in the sebaceous duct, storage of sebum in the follicular reservoir, discharge through the follicular opening and spreading over the stratum corneum [Pierard, Dermatology, vol. 196, pages 126-129 (1998)]. Most sebaceous glands open out into the hair follicle. Some free sebaceous glands open directly onto the skin surface. These include Meibomian glands on the eyelids, Tysons glands on the foreskin and Fordyces spots on the upper lip. Sebum is produced when the sebaceous gland disintegrates. The cells take about a week from formation to discharge. Sebum is a complex and variable mixture of lipids including: Glycerides, Free fatty acids, Wax esters, Squalene, Cholesterol esters, and Cholesterol [Stewart, M. E., Semin. Dermatol. 11, 100-105 (1992)]. The action of bacterial lipases converts a varying portion of the triglycerides to free fatty acids.

The sebocyte constitutes the competent cell of the sebaceous gland. The production of sebum is associated with the program of terminal differentiation of this cell. During this differentiation, the metabolic activity of the sebocyte is essentially centered around the biosynthesis of lipids (lipogenesis), and more precisely on the neosynthesis of fatty acids and the squalene. A compound making it possible to reduce the production of the lipids constituting sebum, by the cells of the sebaceous gland (sebocytes), would therefore be of definite value for the treatment of oily skin. It will also be useful for the reduction of excess skin oil, for example, from acne. Since some of the fatty acids required for this neosynthesis may be derived from triglycerides, a lipase inhibitor such as a saponin or sapogenin could inhibit the neosynthesis of such fatty acids. However, this is just the theory at this juncture, as no prior art exists to claim the lipase inhibition by sugar esters of polycyclic polyisoprenoids upon their topical application. The exact mechanism of the present invention is thus unknown. This lack of scientific knowledge, however, is not to reduce the utility of the present invention in any manner.

Saponins have been reported to possess many useful applications in the prior art. Ramberg et al. have discussed history and uses of *Dioscora* plant, which contains several saponins [Glycoscience and Nutrition, Vol. 3, pages 1-5 (2002)].

Diosgenin has been described as an anti-inflammatory (Yamada et al., Am. J. Physiol., 273:G355-G364, 1997); as a slimming agent, by virtue of its action on adipocytes (WO 00/30603); as a collagenase inhibitor and as an antimicrobial agent which can be used in the treatment of various pathological conditions with an infectious component, including acne and seborrheic dermatitis (DE-198 41 795). Hecogenin and tigogenin, from *Agave americana*, have been reported to possess anti-inflammatory benefits [Peana et al., Planta Med., 63, 199-202 (1997)]. Diosgenin has been reported to suppress 12-lipoxigenase activity [Nappez et al., Cancer Lett., vol. 4, pages 133-140 (1995)].

Cutaneous aging has been treated with various compositions comprising sapogenins, including diosgenin (U.S. Patent application Ser. No. 20020028186; U.S. Pat. No. 6,331,535; FR-2 811 561; and FR-2 811 567). Kim et al. (WO2005070436) disclose an inhibitor for the biosynthesis of gelatinase comprising ginsenoside F1 (20-O-beta-D-glucopyranosyl-20 (S)-protopanaxatriol) or compound K (20-O-beta-D-glucopyranosyl-20 (S)-protopanaxadiol), which is a chief metabolite of ginseng saponin, as an active ingredient; and a cosmetic/medical composition for the prevention of skin aging.

Alexis (U.S. Pat. No. 6,607,765) discloses therapeutic compositions made from the herb *Tribulus terrestris* and methods of making and using the same are provided. The therapeutic compositions include an enriched extract having an increased spirostanol saponin content that is prepared from the harvested *Tribulus terrestris*. The enriched extract is prepared using discrete hydrolysis, separation and enrichment steps. The resulting therapeutic may be combined with a cream base and is useful for treating bacterial, fungal, and viral infections, particularly gynecologic infections. This product was also found to be very successful in suppository form for the treatment of vulvo-vaginal, vulvo-hemorrhoidal and colonic conditions.

U.S. Patent application ser. no. 20030235599 (Besne) relates to a composition containing a sapogenin that is suitable for topical application to the skin for the smoothing out of wrinkles and fine lines.

U.S. Patent application ser. no. 20030152597 (Liviero) relates to a sapogenin or of a natural extract containing it to prevent the signs of ageing of the skin, in particular the loss of elasticity and/or tonicity of the skin and/or the formation of wrinkles and fine lines, by inhibiting the activity of Collagenases.

U.S. Pat. No. 6,878,367 (Picard et al.) disclose the combination of a sapogenin or a derivative or natural extract containing the same, and at least one xanthine base are useful for preventing or combating cellulite and/or for refining the figure or the contours of the face.

U.S. Patent application ser. no. 20030211185 and 2005112218 (Alexis) discloses a spirostanol saponin that is prepared from the harvested *Tribulus terrestris*. The enriched extract is prepared using discrete hydrolysis, separation and enrichment steps. The resulting therapeutic is useful for treating bacterial, fungal, and viral infections, particularly gynecologic infections. The antibacterial benefits of sapogenins are also claimed to treat acne (DE 198-41-795).

Zhong et al. (CN1563074) disclose a steroid saponin compound, and provides its general formula. Said compound contains the straight-chain or branched chain glycoside formed from trisaccharide. Said invention also relates to preparation method of said compound and medicine composite using said compound as active component, and application of said medicine composite containing said invented compound for preparing medicine for curing superficial fungus infection and deep fungus infection.

*Dioscorea tokoro* extract has been described as effective for moisturizing the skin and thus softening it. Thus, document JP-10 194 947 discloses an extract of *Dioscorea tokoro* prepared by extraction using water. This extract, which contains a mucopolysaccharide of molecular weight of 2,000,000, is described as being of use for improving the suppleness and the moisturization of the skin. The glycoproteins, which it contains, are also thought to have a suppressive effect on sebaceous secretion.

U.S. Pat. No. 5,057,502 (Walsh) similarly disclose juniper extract materials that are useful in the thinning of heavy oily, greasy secretions and giving symptom relief in human acne and other conditions of thickened secretions. The molecular structure of the biologically active molecule was shown to be an acidic polysaccharide, related to pectin (a linear polygalacturonic acid).

Anti-obesity benefits of dioscin and diosgenin, obtained from *Dioscora nipponica*, have been reported [Kwon et al., Biosci. Biotechnol. Biochem., 67, 1451-1456 (2003)]. The anti-obesity benefits are claimed to originate from lipase-inhibiting activity in the digestive system of rodents, thus inhibiting triglyceride absorption. The lipase inhibition by sugar esters of polycyclic polyisoprenoids on topical application has not been reported. Anti-hypercholesteramic activity of sapogenins is also described by Ma et al. [Zhongguo Zhong Yao Za Zhi, vol. 27, pages 528-531 (2002)]. The saponins from garlic act as modifiers of cardiovascular disease due to their cholesterol lowering effect [Matsuura, Journal of Nutrition, vol. 131, pages 100S-1005S (2001)]. U.S. Patent application ser. no. 20030119428 (Davis et al.) provides a treatment of obesity using sterol or 5-α-stanol absorption inhibitors. U.S. Pat. No. 6,150,336 (Deninno et al.) discloses steroidal glycoside derivatives useful as hypocholesteramic agents and anti-atherosclerosis agents. However, as Deninno et al. point out, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. U.S. Pat. Nos. 4,602,003 and 4,602,005 disclose certain steroidal glycosides, in particular 3-O-(beta-D-glucopyranosyl)-tigogenin and 3-O-(beta-D-cellobiosyl)-tigogenin and their use for the control of hypercholesterolemia. 3-O-(beta-D-Cellobiosyl)-tigogenin has superior hypocholesteramic activity when compared to, for example, cholestyramine. PCT publication WO 93/07167 discloses several steroidal glycosides in particular 3-O-(5-C-hydroxymethyl-L-arabino-hexopyranosyl)-tigogenin and 3-O-(5-C-hydroxymethyl-L-arabino-hexopyranosyl)-diosgenin and their use in the control of hypercholesterolemia.

Corbier et al. [International Journal of Oncology, vol. 2, pages 899-905 (2003)] have reported the anti-proliferative and apoptosis (cancer treatment) benefits of several sapogenins. Aculeoside B, a spirostanol saponin from *Ruscus aculeatus*, inhibits the growth of leukemia HL-60 cells [Mimaki et al., J. Nat. Prod., vol. 61, pages 1279-1282 (1998)]. Vijay et al. (WO2005063790) disclose a novel saponin tigogenin penta glycoside isolated from the aerial parts of *Chlorophytum nimonii* and a process for the isolation thereof as well as its use in anti-hyperglycemic and hypolipidemic activities.

Neurodegenerative disorders, cognitive dysfunction, non-cognitive neurodegeneration, non-cognitive neuromuscular degeneration, and receptor loss in the absence of cognitive, neural and neuromuscular impairment have been treated with steroidal sapogenins (U.S. Patent application ser. nos. 20050130948, Rees et al.; 20040147495, Barraclough at al., 20040081709, Xia et al.). Alzheimer's disease has been treated with saponins (U.S. Pat. No. 6,812,213; Xia et al.).

U.S. Pat. No. 6,905,714 (Ong et al.) discloses a preparation of *Eucommia ulmoides* prepared by ethanol extraction that is useful for modulating a steroid-mediated physiological condition, wherein the steroid-mediated physiological condition is mediated by an androgen or by androgen receptor, for example, male sexual development, secondary sexual development, anabolic processes, male sex drive, skin condition, hair growth, physical stamina or lipid metabolism. The effect of skin condition modulation, for example effect on sebum production by topical application of these extracts in the absence of a steroid-mediated physiological condition was not disclosed by Ong et al.

Saponins have been reported to possess detergency properties, as claimed by Sprague et al. (U.S. patent application ser. No. 2005090565). Saponins can thus remove surface oil and sebum, for example on skin by their detergency action. However, their effect on reducing the sebum and oil biosynthesis in skin was not reported by Sprague at al.

The above discussion of the prior art reveals that none of the sugar esters of polycyclic polyisoprenoids, and/or the topical applications thereof, has been claimed in the prior art.

In fact, Rubisntenn et al. (JP2003300862) specifically claim a cosmetic composition containing a sapogenin selected from diosgenin and hecogenin or a sapogenin-containing plant extract that is used as a treatment agent for the hyposeborrheic dry skin or dry scalp. The sapogenin or the sapogenin-containing plant extract can also be used for the dermatological treatment method for diseases related to the hyposeborrheic dry skin. These can be applied to the treatment of skin dry out, especially to the skin of females after climacteric. However, these authors do not disclose any sugar esters of said sapogenin.

The present invention discloses certain sugar esters of polycyclic polyisoprenoids [FIG. 1], and compositions based on said polyisoprenoids. The sugar esters of the polycyclic polyisoprenoids of the present invention provide both an enhanced delivery and bioavailablity of said polyisoprenoids from both topical and ingestible compositions. These are useful, among other benefits, for applications for the treatment of skin condition, and skin ailments resulting from age-related, environmental-triggered, and/or hormonal misbalance disorders.

[FIG. 1].

The structures of polycyclic polyisoprenoid substituent, ($R^1$ in FIG. 1), are illustrated in [FIG. 2 and FIG. 3].

[FIG. 2].

[FIG. 3].

The sugar esters of polycyclic polyisoprenoids of the present invention include sugar esters of sapogenins, steroids, and triterpenoids, select examples of which are illustrated in [FIG. 4].

[FIG. 4].

A number of new, biologically active polycyclic triterpenes have been reported in recent years; the gluconate esters of important examples of which, in accordance to the present invention, are included in [FIG. 5].

[FIG. 5].

The process for the sugar esters of polycyclic polyisoprenoids of the present invention comprises (i) the combining of a sugar lactone and a phytosterol, and (ii) a solvent or reaction medium agent, and (iii) heating at 50 to 120 C [FIG. 6].

[FIG. 6].

The said esters of phytosterols of the present invention are made, as mentioned above, by the reaction of polycyclic polyisoprenoids having a free hydroxyl group, preferably a primary or a secondary hydroxyl, with a sugar lactone. This reaction is best carried out under acidic pH conditions, preferably from a pH of 2.5 to 6.5, and most preferably from a pH of 3.5 to 5.5. A solvent medium can be used, which is selected from, but not limited to water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methylpyrrolidone, pyrrolidone, methyl lactate, ethyl lactate, propyl lactate, isopropyl lactate, butyl lactate, isobutyl lactate, t-butyl lactate, pentyl lactate, neopentyl lactate, isopentyl lactate, hexyl lactate, ethylhexyl lactate, glycerol lactate, benzyl lactate, triethyl citrate, trimethyl citrate, tributyl citrate, acetyl triethyl citrate, acetyl tributyl citrate, trihexyl citrate, butyl trihexyl citrate, stearyl citrate, diethyl tartrate, dimethyl tartrate, ethyl mandelate, ethyl salicylate, methyl salicylate, ethyl glycolate, and combinations thereof. The suitable reaction temperature is from 50 to 120 degrees Celsius (C), preferably from 60 to 100 C, and most preferably from 70 to 90 C.

The said polycyclic polyisoprenoids include, but not limited to Dioscin, Diosgenin, Hecogenin, Heconin, Tigogenin, Tigonin, Gitogenin, Chlorogenin, Eruboside, Protoeruboside, Manogenin, Shlorogenin, Hainangenin, Protodioscin, Protosmilagenin, Aculeoside, Smilagenin, Sarsapogenin, Yamogenin, Yuccagenin, Gracillin, Divergioic acid, Sericic acid, Asiatic acid, Arjunic acid, Tormetic acid, Ursolic acid, Madecassic acid, Glycyrrhizic acid, Glycyrrhetinic acid, Boswellic acid, Moronic acid, Ruscogenin, guggul sterols, forskohlin, forskohlin isomers, garcinol, Platanic acid, Dihydrobetulinic acid, Uvaol, Hydroxymapronic acid, Celasdin, Suberosol, Kauranoic acid, Linearol, Prostratin, Deoxyphorbol, Andrographolide, Nortripterifordin, Tall oil (pine) sterols, and Sativoside.

The said sugar lactones include, but not limited to gluconolactone, galactonolactone, glucuronolactone, galacturonolactone, gulonolactone, glucoheptonolactone, ribonolactone, saccharolactone, hydroxycitric acid lactone, pantoyllactone, mannonolactone, *Garcinia* lactone, arabinolactone, isopropylidene Ribonolactone, Glucooctanolactone, Erythronolactone, isocitric acid lactone, Glyceromannoheptonolactone, and galactoheptonolactone.

The sugar esters of polycyclic polyisoprenoids of the present invention can be obtained, via chemical process disclosed herein, also from polycyclic polyisoprenoids obtained from various plant sources, such as *Ruscus aculeatus*, Garlic, *Dioscora, Tribulus terrestris*, Alfalfa, *Chlorophytum nimonii*, and *Agave*. Among these, mention may be made of the *Dioscorea composita, Dioscorea deltoides, Dioscorea floribunda, Dioscorea sylvatica, Dioscorea spiculiflora* and *Dioscorea villosa* species.

The sugar esters of polycyclic polyisoprenoids of the present invention can also be obtained and used in an extract form. The expression "plant extracts" is intended to mean any plant extract containing one or more of these saponins and/or sapogenins. Diosgenin can be extracted from the tubers of certain *Dioscorea* using a method comprising successively: hydrolysis, under hot conditions, of the heterosides in inorganic acid medium (optionally after fermentation and drying of the tubers); and filtration of the insoluble fraction, which is then neutralized, washed and treated with an apolar solvent. Hecogenin can be extracted from the leaves of *Agave Sisalana*. Such extracts can be further refined and obtained in a higher chemical purity by usual extraction and purification methods, for example, U.S. Pat. No. 3,981,867 (Beauvoir). Other extraction methods can also be used, for example $CO_2$ extraction. The extracted compositions can then be converted into corresponding sugar esters by the chemical process of the present invention.

In several of the above cases where an extract is used directly in the preparation of corresponding sugar ester derivatives according to the present invention, said extracts can contain several components, for example, guggul lipids from guggul (*Commiphora wightii*) contain several guggul sterols that includes Z-guggul sterol, E-guggul sterol, guggul sterol -I, guggul sterol -II, guggul sterol -III, and guggul sterol -IV; in such cases a mixture of sugar esters of said sterols is obtained. Guggul sterols have achieved prominence due to their anti-inflammatory, anti-rheumatic, anti-arthritis, hypo-cholesteremic, hypolipidemic and anti-fertility activities. Recent prior art references relative to separation of guggul components and their biological properties include U.S. Pat. No. 6,086,889; U.S. pat application Ser. Nos. 20050163872 and 20040253327; and WO 2005072761. Another terpenoid, forskohlin, similarly occurs naturally as a mixture of several components that includes forskohlin, deacetylforskohlin, 9-deoxyforskohlin, 1,9-deoxyforskohlin, and 1,9-dideoxy-7-deacetylforskohlin; in this case a mixture of sugar esters is obtained. Forskohlins are well known for their weight reduction benefits. As an example, the reaction of gluconolactone with guggul sterols results in the formation of a mixture of guggul sterol gluconates (FIG. 7), which can be used directly in the topical compositions of the present invention.

[FIG. 7].

The sugar esters of polycyclic polyisoprenoids of the present invention are not limited only to steroids, sapogenins, and terpenoids. Almost all cyclic isoprenoids that have a hydroxyl group can be converted into their corresponding sugar esters by the process of the present invention. Important polyisoprenoids, such as garcinol and forskohlin, can be converted into their corresponding sugar esters [FIG. 8]. Garcinol has attracted much clinical attention of late (Majeed, U.S. patent application Ser. No. 20080207950).

[FIG. 8].

Among other cyclic polyisoprenoids, pine (tall oil) sterols have attracted much recent attention due to their anti-HIV and antiviral properties. The reaction of said pine sterols with a sugar lactone, for example gluconolactone, results in the formation of a mixture of pine sterol sugar esters in accordance to the present invention [FIG. 9].

[FIG. 9].

The sugar esters of polycyclic polyisoprenoids of the present invention include, but not limited to diosgenin gluconate, diosgenin galactonate, diosgenin glucuronate, diosgenin saccharate, diosgenin pantoylate, diosgenin mannonate, diosgenin garcinate, diosgenin hydroxycitrate, diosgenin arabinate, diosgenin isopropylidene ribonate, diosgenin glucooctanate, diosgenin erythronate, diosgenin isocitrate, diosgenin glyceromannoheptonate, diosgenin galactoheptonate, tigogenin gluconate, tigogenin galactonate, tigogenin glucuronate, tigogenin saccharate, tigogenin pantoylate, tigogenin mannonate, tigogenin garcinate, tigogenin hydroxycitrate, tigogenin arabinate, tigogenin isopropylidene ribonate, tigogenin glucooctanate, tigogenin erythronate, tigogenin isocitrate, tigogenin glyceromannoheptonate, tigogenin galactoheptonate, hecogenin gluconate, hecogenin galactonate, hecogenin glucuronate, hecogenin saccharate, hecogenin pantoylate, hecogenin mannonate, hecogenin garcinate, hecogenin hydroxycitrate, hecogenin arabinate, hecogenin isopropylidene ribonate, hecogenin glucooctanate, hecogenin erythronate, hecogenin isocitrate, hecogenin glyceromannoheptonate, hecogenin galactoheptonate, gitogenin gluconate, gitogenin galactonate, gitogenin glucuronate, gitogenin saccharate, gitogenin pantoylate, gitogenin mannonate, gitogenin garcinate, gitogenin hydroxycitrate, gitogenin arabinate, gitogenin isopropylidene ribonate, gitogenin glucooctanate, gitogenin erythronate, gitogenin isocitrate, gitogenin glyceromannoheptonate, gitogenin galactoheptonate, chlorogenin gluconate, chlorogenin galactonate, chlorogenin glucuronate, chlorogenin saccharate, chlorogenin pantoylate, chlorogenin mannonate, chlorogenin garcinate, chlorogenin hydroxycitrate, chlorogenin arabinate, chlorogenin isopropylidene ribonate, chlorogenin glucooctanate, chlorogenin erythronate, chlorogenin isocitrate, chlorogenin glyceromannoheptonate, chlorogenin galactoheptonate, manogenin gluconate, manogenin galactonate, manogenin glucuronate, manogenin saccharate, manogenin pantoylate, manogenin mannonate, manogenin garcinate, manogenin hydroxycitrate, manogenin arabinate, manogenin isopropylidene ribonate, manogenin glucooctanate, manogenin erythronate, manogenin isocitrate, manogenin glyceromannoheptonate, manogenin galactoheptonate, shlorogenin gluconate, shlorogenin galactonate, shlorogenin glucuronate, shlorogenin saccharate, shlorogenin pantoylate, shlorogenin mannonate, shlorogenin garcinate, shlorogenin hydroxycitrate, shlorogenin arabinate, shlorogenin isopropylidene ribonate, shlorogenin glucooctanate, shlorogenin errythronate, shlorogenin isocitrate, shlorogenin glyceromannoheptonate, shlorogenin galactoheptonate, hainangenin gluconate, hainangenin galactonate, hainangenin glucuronate, hainangenin saccharate, hainangenin pantoylate, hainangenin mannonate, hainangenin garcinate, hainangenin hydroxycitrate, hainangenin arabinate, hainangenin isopropylidene ribonate, hainangenin glucooctanate, hainangenin errythronate, hainangenin isocitrate, hainangenin glyceromannoheptonate, hainangenin galactoheptonate, sarsapogenin gluconate, sarsapogenin galactonate, sarsapogenin glucuronate, sarsapogenin saccharate, sarsapogenin pantoylate, sarsapogenin mannonate, sarsapogenin garcinate, sarsapogenin hydroxycitrate, sarsapogenin arabinate, sarsapogenin isopropylidene ribonate, sarsapogenin glucooctanate, sarsapogenin errythronate, sarsapogenin isocitrate, sarsapogenin glyceromannoheptonate, sarsapogenin galactoheptonate, yamogenin gluconate, yamogenin galactonate, yamogenin glucuronate, yamogenin saccharate, yamogenin pantoylate, yamogenin mannonate, yamogenin garcinate, yamogenin hydroxycitrate, yamogenin arabinate, yamogenin isopropylidene ribonate, yamogenin glucooctanate, yamogenin errythronate, yamogenin isocitrate, yamogenin glyceromannoheptonate, yamogenin galactoheptonate, yuccagenin gluconate, yuccagenin galactonate, yuccagenin glucuronate, yuccagenin saccharate, yuccagenin pantoylate, yuccagenin mannonate, yuccagenin garcinate, yuccagenin hydroxycitrate, yuccagenin arabinate, yuccagenin isopropylidene ribonate, yuccagenin glucooctanate, yuccagenin errythronate, yuccagenin isocitrate, yuccagenin glyceromannoheptonate, yuccagenin galactoheptonate, divergioic acid gluconate, divergioic acid galactonate, divergioic acid glucuronate, divergioic acid saccharate, divergioic acid pantoylate, divergioic acid mannonate, divergioic acid garcinate, divergioic acid hydroxycitrate, divergioic acid arabinate, divergioic acid isopropylidene ribonate, divergioic acid glucooctanate, divergioic acid errythronate, divergioic acid isocitrate, divergioic acid glyceromannoheptonate, divergioic acid galactoheptonate, sericic acid gluconate, sericic acid galactonate, sericic acid glucuronate, sericic acid saccharate, sericic acid pantoylate, sericic acid mannonate, sericic acid garcinate, sericic acid hydroxycitrate, sericic acid arabinate, sericic acid isopropylidene ribonate, sericic acid glucooctanate, sericic acid errythronate, sericic acid isocitrate, sericic acid glyceromannoheptonate, sericic acid galactoheptonate, asiatic acid gluconate, asiatic acid galactonate, asiatic acid glucuronate, asiatic acid saccharate, asiatic acid pantoylate, asiatic acid mannonate, asiatic acid garcinate, asiatic acid hydroxycitrate, asiatic acid arabinate, asiatic acid isopropylidene ribonate, asiatic acid glucooctanate, asiatic acid errythronate, asiatic acid isocitrate, asiatic acid glyceromannoheptonate, asiatic acid galactoheptonate, tormetic acid gluconate, tormetic acid galactonate, tormetic acid glucuronate, tormetic acid saccharate, tormetic acid pantoylate, tormetic acid mannonate, tormetic acid garcinate, tormetic acid hydroxycitrate, tormetic acid arabinate, tormetic acid isopropylidene ribonate, tormetic acid glucooctanate, tormetic acid errythronate, tormetic acid isocitrate, tormetic acid glyceromannoheptonate, tormetic acid galactoheptonate, ursolic acid gluconate, ursolic acid galactonate, ursolic acid glucuronate, ursolic acid saccharate, ursolic acid pantoylate, ursolic acid mannonate, ursolic acid garcinate, ursolic acid hydroxycitrate, ursolic acid arabinate, ursolic acid isopropylidene ribonate, ursolic acid glucooctanate, ursolic acid errythronate, ursolic acid isocitrate, ursolic acid glyceromannoheptonate, ursolic acid galactoheptonate, madecassic acid gluconate, madecassic acid galactonate, madecassic acid glucuronate, madecassic acid saccharate, madecassic acid pantoylate, madecassic acid mannonate, madecassic acid garcinate, madecassic acid hydroxycitrate, madecassic acid arabinate, madecassic acid isopropylidene ribonate, madecassic acid glucooctanate, madecassic acid errythronate, madecassic acid isocitrate, madecassic acid glyceromannoheptonate, madecassic acid galactoheptonate, glycyrrhizic acid gluconate, glycyrrhizic acid galactonate, glycyrrhizic acid glucuronate, glycyrrhizic acid saccharate, glycyrrhizic acid pantoylate, glycyrrhizic acid mannonate, glycyrrhizic acid garcinate, glycyrrhizic acid hydroxycitrate, glycyrrhizic acid arabinate, glycyrrhizic acid isopropylidene ribonate, glycyrrhizic acid glucooctanate, glycyrrhizic acid errythronate, glycyrrhizic acid isocitrate, glycyrrhizic acid glyceromannoheptonate, glycyrrhizic acid galactoheptonate, glycyrrhetinic acid gluconate, glycyrrhetinic acid galactonate, glycyrrhetinic acid glucuronate, glycyrrhetinic acid saccharate, glycyrrhetinic acid pantoylate, glycyrrhetinic acid mannonate, glycyrrhetinic acid garcinate, glycyrrhetinic acid hydroxycitrate, glycyrrhetinic acid arabinate, glycyrrhetinic acid isopropylidene ribonate, glycyrrhetinic acid glucooctanate, glycyrrhetinic acid errythronate, glycyrrhetinic acid isocitrate, glycyrrhetinic acid glyceromannoheptonate, glycyrrhetinic acid galactoheptonate, boswellic acid gluconate, boswellic acid galactonate, boswellic acid glucuronate, boswellic acid saccharate, boswellic acid pantoylate, boswellic acid mannonate, boswellic acid garcinate, boswellic acid hydroxycitrate, boswellic acid arabinate, boswellic acid isopropylidene ribonate, boswellic acid glucooctanate, boswellic acid errythronate, boswellic acid isocitrate, boswellic acid glyceromannoheptonate, boswellic acid galactoheptonate, moronic acid gluconate, moronic acid galactonate, moronic acid glucuronate, moronic acid saccharate, moronic acid pantoylate, moronic acid mannonate, moronic acid garcinate, moronic acid hydroxycitrate, moronic acid arabinate, moronic acid isopropylidene ribonate, moronic acid glucooctanate, moronic acid errythronate, moronic acid isocitrate, moronic acid glyceromannoheptonate, moronic acid galactoheptonate, ruscogenin gluconate, ruscogenin galactonate, ruscogenin glucuronate, ruscogenin saccharate, ruscogenin pantoylate, ruscogenin mannonate, ruscogenin garcinate, ruscogenin hydroxycitrate, ruscogenin arabinate, ruscogenin isopropylidene ribonate, ruscogenin glucooctanate, ruscogenin errythronate, ruscogenin isocitrate, ruscogenin glyceromannoheptonate, ruscogenin galactoheptonate, smilagenin gluconate, smilagenin galactonate, smilagenin glucuronate, smilagenin saccharate, smilagenin pantoylate, smilagenin mannonate, smilagenin garcinate, smilagenin hydroxycitrate, smilagenin arabinate, smilagenin isopropylidene ribonate, smilagenin glucooctanate, smilagenin errythronate, smilagenin isocitrate, smilagenin glyceromannoheptonate, smilagenin galactoheptonate, guggul sterols gluconate, guggul sterols galactonate, guggul sterols glucuronate, guggul sterols saccharate, guggul sterols pantoylate, guggul sterols mannonate, guggul sterols garcinate, guggul sterols hydroxycitrate, guggul sterols arabinate, guggul sterols isopropylidene ribonate, guggul sterols glucooctanate, guggul sterols errythronate, guggul sterols isocitrate, guggul sterols glyceromannoheptonate, guggul sterols galactoheptonate, forskohlin gluconate, forskohlin galactonate, forskohlin glucuronate, forskohlin saccharate, forskohlin pantoylate, forskohlin mannonate, forskohlin garcinate, forskohlin hydroxycitrate, forskohlin arabinate, forskohlin isopropylidene ribonate, forskohlin glucooctanate, forskohlin erythronate, forskohlin isocitrate, forskohlin glyceromannoheptonate, forskohlin galactoheptonate, garcinol gluconate, garcinol galactonate, garcinol glucuronate, garcinol saccharate, garcinol pantoylate, garcinol mannonate, garcinol garcinate, garcinol hydroxycitrate, garcinol arabinate, garcinol isopropylidene ribonate, garcinol glucooctanate, garcinol erythronate, garcinol isocitrate, garcinol glyceromannoheptonate, garcinol galactoheptonate, tall oil (pine) sterol gluconate, tall oil (pine) sterol galactonate, tall oil (pine) sterol glucuronate, tall oil (pine) sterol saccharate, tall oil (pine) sterol pantoylate, tall oil (pine) sterol mannonate, tall oil (pine) sterol garcinate, tall oil (pine) sterol hydroxycitrate, tall oil (pine) sterol arabinate, tall oil (pine) sterol isopropylidene ribonate, tall oil (pine) sterol glucooctanate, tall oil (pine) sterol erythronate, tall oil (pine) sterol isocitrate, tall oil (pine) sterol glyceromannoheptonate, tall oil (pine) sterol galactoheptonate, andrographolide gluconate, andrographolide galactonate, andrographolide glucuronate, andrographolide saccharate, andrographolide pantoylate, andrographolide mannonate, andrographolide garcinate, andrographolide hydroxycitrate, andrographolide arabinate, andrographolide isopropylidene ribonate, andrographolide glucooctanate, andrographolide erythronate, andrographolide isocitrate, andrographolide glyceromannoheptonate, andrographolide galactoheptonate, and additional compounds that are made by a combination of polycyclic polyisoprenoids included in paragraph 66 and sugar lactones in paragraph 67 according to the present invention, and combinations thereof.

The sugar esters of the present invention are for topical application, among their other applications. The topical application is for the treatment of dermatological disorders, which includes age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

The amount of phytosterol sugar esters, which can be used topically according to the present invention, depends of course on the desired effect and can therefore vary within a large range, this amount being within the skill of the ordinary artisan in view of this disclosure. To give an order of magnitude, the saponin or sapogenin can be used in an amount representing from 0.0001% to 5.0% of the total weight of a composition, preferably in an amount representing from 0.01% to 2.0% of the total weight of the composition. The plant extract containing saponin or sapogenin can be used in an amount representing from 0.0001% to 20% of the total weight of a composition, depending on the % solids content of the plant extract and the amount and nature of the extraction solvent present in such extract.

It has additionally been discovered by the present inventor that the inclusion of zinc salts of certain hydroxy acids in combination with sugar esters of sugar esters of polycyclic polyisoprenoids of the present invention synergistically increase the sebum and skin oil reducing benefits of such sugar esters of sugar esters of polycyclic polyisoprenoids. The examples of such zinc salts of hydroxy acids include zinc Hydroxycitrate; zinc Hydroxybenzoate, zinc salicylate, zinc mandelate, zinc lactate, zinc glycolate, zinc malate, zinc tetronate, zinc tartrate, and combinations thereof. This is highly unexpected and surprising since zinc salts, such as zinc Salicylate, have been reported to possess antibacterial benefits (U.S. Patent application ser. no. 20050019288, Lemoine; U.S. Pat. No. 6,846,846, Modak et al; U.S. Pat. No. 6,656,456; Dodd et al.); and anti-irritant benefits (U.S. Pat. No. 5,985,918; Modak et al.). The Topical treatment benefits of such zinc salts; either alone, or in synergistic combinations with sugar esters of saponin or sapogenin, has not been disclosed in the prior art.

Synergistic benefits are also noted when a Citrate Lyase enzyme inhibitor agent is included in combination with sugar esters of sugar esters of polycyclic polyisoprenoids of the present invention. The examples of such agents include Forskohlin, *Coleus forskohlii* extract, *Momordica Charantia* extract, Charantins, Momordicosides, Hydroxycitric acid, *Garcinia cambogia* extract, Phaseolamin, *Phaseolus vulgaris* extract, Synephrine, Hordenine, Octopamine, Tyramine, n-Methyltyramine, and combinations thereof. The Topical treatment benefits of such Citrate Lyase enzyme inhibitors, either alone, or in synergistic combinations with a sugar esters of saponin or sapogenin, have not been disclosed in the prior art.

For topical application to the skin, the polycyclic polyisoprenoid esters of the present invention may be provided in any cosmetic or pharmaceutical form normally used in the cosmetics and dermatological fields, and it may in particular be in the form of an aqueous, optionally gelled, solution, of a dispersion of the optionally two-phase lotion type, of an emulsion obtained by dispersion of a fatty phase (oil) in an aqueous phase (O/W) or vice versa (W/O), of a triple emulsion (W/O/W or O/W/O) or of a vesicular dispersion of the ionic and/or nonionic type. These compositions may be prepared according to the usual methods. This composition may be more or less fluid and have the appearance of a cream, an ointment, a milk, a lotion, a serum, a paste, and a mousse. It may optionally be applied in the form of an aerosol. It may also be provided in solid form, in particular in the form of a stick. It may be used as a care product and/or as a make-up product for the skin. It may also be used as a shampoo or a conditioner.

Polycyclic polyisoprenoid esters of the present invention can be formulated in various cosmetic and pharmaceutical consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system can be traditional water and oil emulsions, suspensions, colloids, micro emulsions, clear solutions, suspensions of nanoparticles, emulsions of nanoparticles, or anhydrous compositions.

The compositions that contain the compound of the present invention may also contain adjuvants which are used in the cosmetics field, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants may be those conventionally used in the field considered. These adjuvants, depending on their nature, can be introduced into the fatty phase, into the aqueous phase or into the lipid vesicles. In addition, moisturizers may complete the effect obtained using the sapogenins according to the invention and anti-inflammatory agents are also useful.

The application of polycyclic polyisoprenoid esters of the present invention can be in several areas of consumer interest, some of which include control of excess facial oil associated with acne, control of excess oil on scalp associated with dandruff, and control of excess body and underarm oil associated with body and underarm malodor.

Dandruff is the result of the normal growing process of the skin cells of the scalp. Shedding of dead skin cells from the scalp at an excessive rate is the result of the normal growing process of the skin cells of the scalp. In a normal scalp, the process of sloughing off old cells and manufacturing of their replacements is very orderly and complete. In the dandruff scalp, there is mass disorder and often the departing cells are not dead before leaving the scalp. Contrary to popular theory, although bacteria may aggravate a dandruff condition, bacteria do not cause the initial problem. Most medical authorities consider dandruff, even the mildest forms, to be a type of scalp or skin related disease. Clinically, one description of dandruff is Seborrhea Capitos or excessive sebum production of the scalp. Today most skin specialists agree that dandruff is associated with a tiny fungus called *Pityrosporum* ovale, or *P. ovale* for short. This fungus lives on our bodies and scalp all the time, usually without causing a problem. It has been theorized that *P. ovale* metabolizes excess oil on scalp, which results in the formation of lower molecular weight fatty acids that cause skin irritation leading to dandruff. Although the present inventor has not studied the effect of the compounds of the present invention on dandruff itself, the compounds of the present invention have been found to reduce the excess sebum or oil on scalp.

Additional cosmetically or pharmaceutically beneficial ingredients can also be included in the formulated compositions of the present invention, which can be selected from skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about C.sub.10 to C.sub.22, long chain fatty amines from about C.sub.10 to C.sub.22, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, crosslinked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface-active agents include surfactants, which typically provide detersive functionality to a formulation or act simply as wetting agents. Surface-active agents can generally be categorized as anionic surface-active agents, cationic surface-active agents, non-ionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated C12-38 n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL as described in U.S. Pat. No. 2,528,378. Other sarcosinates and sarcosinate derivatives that can be found in the CTFA Cosmetic Ingredient Handbook, Fifth Edition, 1988, are incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions that contain Topical treatment agents of the present invention may include long chain fatty amines from about $C_{10}$ to $C_{22}$ and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable compositions that contain Topical treatment agents of the present invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable compositions that contain Topical treatment agents of the present invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions that contain Topical treatment agents of the present invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end-blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions that contain polycyclic polyisoprenoid esters of the present invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane. 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions that contain polycyclic polyisoprenoid esters of the present invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the present invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions that contain polycyclic polyisoprenoid esters of the present invention may include volatile hydrocarbon oils. The volatile hydrocarbon comprises from about C-6 to C-22 atoms. A preferred volatile hydrocarbon is an aliphatic hydrocarbon having a chain length from about C-6 to C-16 carbon atoms. An example of such compound includes isohexadecane, under the trade name Permethyl 101A, available from Presperse, South Plainfield, N.J., USA. Another example of a preferred volatile hydrocarbon is C-12 to C-14 isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions that contain polycyclic polyisoprenoid esters of the present invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable compositions that contain polycyclic polyisoprenoid esters of the present invention may include one or more rheological modifiers. The rheological modifiers that can be used in this invention include, but are not limited to high molecular weight crosslinked homopolymers of acrylic acid, and Acrylates/C10-30 Alkyl Acrylate Crosspolymer, such as the Carbopol and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropylttrimonium chloride/ acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition that contain polycyclic polyisoprenoid esters of the present invention may include one or more antioxidants, which include, but are not limited to ascorbic acid, BHT, BHA, erythorbic acid, bisulfite, thioglycolate, tocopherol, sodium metabisulfite, vitamin E acetate, and sugar palmitate. The anti oxidants will be present at from 0.01 to 5 weight percent, preferably 0.1 to 3 weight percent and most preferably from 0.2 to 2 weight percent of the cosmetically acceptable composition.

The cosmetically acceptable compositions that contain polycyclic polyisoprenoid esters of the present invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl)aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable compositions that contain polycyclic polyisoprenoid esters of the present invention may include one or more preservatives. Example of preservatives, which may be used include, but are not limited to 1,2-dibromo-2,4-dicyano butane (Methyldibromo Glutaronitrile, known as MERGUARD. Nalco Chemical Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, and sodium benzoate, and mixtures thereof.

The cosmetically acceptable compositions that contain polycyclic polyisoprenoid esters of the present invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable compositions that contain polycyclic polyisoprenoid esters of the present invention can be presented in various forms. Examples of such forms include, but are not limited a solution, liquid, cream, emulsion, dispersion, gel, and thickening lotion.

The cosmetically acceptable compositions that contain polycyclic polyisoprenoid esters of the present invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable compositions that contain polycyclic polyisoprenoid esters of the present invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable compositions that contain polycyclic polyisoprenoid esters of the present invention can also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin that contain polycyclic polyisoprenoid esters of the present invention include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions that contain polycyclic polyisoprenoid esters of the present invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions that contain polycyclic polyisoprenoid esters of the present invention for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions that contain polycyclic polyisoprenoid esters of the present invention contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions that contain polycyclic polyisoprenoid esters of the present invention are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the compositions that contain polycyclic polyisoprenoid esters of the present invention may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an acrylate/diacetoneacrylamide copolymer, butyl ester of ethylene/maleic anhydride copolymer, corn starch/acrylamide/sodium acrylate copolymer, diethylene glycolamine/epichlorohydrin/piperazine-copolymer, dodecanedioic acid/cetearyl alcohol/glycol copolymer, copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetically acceptable carrier contained in the cosmetic compositions that contain polycyclic polyisoprenoid esters of the present invention may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion that contain polycyclic polyisoprenoid esters of the present invention may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension that contain polycyclic polyisoprenoid esters of the present invention may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these ingredients.

The formulation of cleansing compositions that contain polycyclic polyisoprenoid esters of the present invention with surfactant may comprise aliphatic alcohol sulfate, aliphatic alcohol ether sulfate, sulfosucinnate monoester, isethionate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

As active agents, it will be advantageous to introduce into the composition used according to the invention at least one compound chosen from: desquamating agents; moisturizers; depigmenting or propigmenting agents; antiglycation agents; NO-synthase inhibitors; agents for stimulating the synthesis of dermal or epidermal macromolecules and/or for preventing their degradation; agents for stimulating the proliferation of fibroblasts and/or keratinocytes or for stimulating the differentiation of keratinocytes; muscle relaxants; tensioning agents; antipollution agents and/or free-radical scavengers; agents acting on the capillary circulation; agents acting on the energy metabolism of cells; and mixtures thereof. Examples of such additional compounds are given below.

Desquamating Agents.

The term "desquamating agent" means any compound capable of acting: either directly on the desquamation by promoting exfoliation, such as beta-hydroxy acids, in particular salicylic acid and its derivatives (including 5-n-octanoyl-salicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol; or on the enzymes involved in the desquamation or degradation of corneodesmosomes, glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; aminosulphonic compounds and in particular (N-2-hydroxyethylpiperazine-N-2-ethane)sulphonic acid (HEPES); 2-oxothiazolidine-4-carboxylic acid (procysteine); α-amino acid derivatives of the type such as glycine (as described in EP-0 852 949, and sodium methyl glycine diacetate sold by BASF under the trade name Trilon M); honey; sugar derivatives such as O-octanoyl-6-D-maltose and N-acetylglucosamine.

Moisturizer.

The term "moisturizer" means: either a compound acting on the barrier function, in order to maintain the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, beta-sitosterol or campesterol), essential fatty acids, 1,2-diacylglycerol, 4-chromanone, pentacyclic triterpenes such as ursolic acid, petroleum jelly and lanolin; or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-.alpha.-benzoyl-L-arginine; or a compound that activates the sebaceous glands, such as DHEA and its derivatives and vitamin D and its derivatives.

Depigmenting or Propigmenting Agent.

The depigmenting agents that may be incorporated into the composition according to the present invention comprise, for example, the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; ascorbic acid and its derivatives, especially sugar glucoside; and plant extracts, in particular extracts of liquorice, of mulberry and of skullcap, without this list being limiting.

Propigmenting agents that may be mentioned include the extract of burnet (*Sanguisorba officinalis*) sold by the company Maruzen, and extracts of chrysanthemum (*Chrysanthemum morifolium*).

Anti-Glycation Agent.

The term "anti-glycation agent" means a compound for preventing and/or reducing the glycation of skin proteins, in particular of dermal proteins such as collagen.

Examples of anti-glycation agents are plant extracts of the Ericacea family, such as an extract of blueberry (*Vaccinium angustifolium*); ergothioneine and its derivatives; and hydroxystilbenes and their derivatives, such as resveratrol and 3,3',5,5'-tetrahydroxystilbene. Resveratrol is particularly preferred for use in this invention.

NO-synthase Inhibitor.

Examples of NO-synthase inhibitors that are suitable for use in the present invention especially comprise a plant extract of the species *Vitis vinifera* which is sold especially by the company Euromed under the name Leucocyanidines de raisins extra, or by the company Indena under the name Leucoselect, or finally by the company Hansen under the name Extrait de marc de raisin; a plant extract of the species *Olea europaea* which is preferably obtained from olive tree leaves and is sold especially by the company Vinyals in the form of a dry extract, or by the company Biologia & Technologia under the trade name Eurol BT; and a plant extract of the species *Gingko biloba* which is preferably a dry aqueous extract of this plant sold by the company Beaufour under the trade name *Gingko biloba* extrait standard.

Agent for Stimulating the Synthesis of Dermal or Epidermal Macromolecules and/or for Preventing their Degradation.

Among the active agents for stimulating dermal macromolecules or for preventing their degradation, mention may be made of those that act: either on collagen synthesis, such as extracts of *Centella asiatica*; asiaticosides and derivatives; ascorbic acid or vitamin C and its derivatives; synthetic peptides such as lamin, biopeptide CL or the palmitoyloligopeptide sold by the company Sederma; peptides extracted from plants, such as the soybean hydrolysate sold by the company Coletica under the trade name Phytokine; and plant hormones such as auxins; or on elastin synthesis, such as the extract of *Saccharomyces cerivisiae* sold by the company LSN under the trade name Cytovitin; and the extract of the alga *Macrocystis pyrifera* sold by the company SECMA under the trade name Kelpadelie; or on glycosaminoglycan synthesis, such as the product of fermentation of milk with *Lactobacillus* vulgaris, sold by the company Brooks under the trade name Biomin yogourth; the extract of the brown alga Padina pavonica sold by the company Alban Muller under the trade name HSP3; and the extract of *Saccharomyces cerevisiae* available especially from the company Silab under the trade name Firmalift or from the company LSN under the trade name Cytovitin; or on fibronectin synthesis, such as the extract of the zooplankton Salina sold by the company Seporga under the trade name GP4G; the yeast extract available especially from the company Alban Muller under the trade name Drieline; and the palmitoyl pentapeptide sold by the company Sederma under the trade name Matrixil; or on metalloprotease (MMP) inhibition, such as, more particularly, MMP 1, 2, 3 or 9. Mention may be made of: retinoids and derivatives, oligopeptides and lipopeptides, lipoamino acids, the malt extract sold by the company Coletica under the trade name Collalift; extracts of blueberry or of rosemary; lycopene; isoflavones, their derivatives or plant extracts containing them, in particular extracts of soybean (sold, for example, by the company Ichimaru Pharcos under the trade name Flavosterone SB), of red clover, of flax, of kakkon, or of sage; or on the inhibition of serine proteases such as leukocyte elastase or cathepsin G. Mention may be made of: the peptide extract of Leguminosa seeds (*Pisum sativum*) sold by the company LSN under the trade name Parelastyl; heparinoids; and pseudodipeptides.

Among the active agents that stimulate epidermal macromolecules, such as fillagrin and keratins, mention may be made especially of the extract of lupin sold by the company Silab under the trade name Structurine; the extract of beech *Fagus sylvatica* buds sold by the company Gattefosse under the trade name Gatuline; and the extract of the zooplankton Salina sold by the company Seporga under the trade name GP4G.

7. Agent for Stimulating the Proliferation of Fibroblasts or Keratinocytes and/or Keratinocyte Differentiation.

The agents for stimulating the proliferation of fibroblasts that may be used in the composition according to the invention may be chosen, for example, from plant proteins or polypeptides, extracts, especially of soybean (for example an extract of soybean sold by the company LSN under the name Eleseryl SH-VEG 8 or sold by the company Silab under the trade name Raffermine); and plant hormones such as giberrellins and cytokinins.

The agents for stimulating keratinocyte proliferation that may be used in the composition according to the invention especially comprise retinoids such as retinol and its esters, including retinyl palmitate; phloroglucinol; extracts of nut cakes sold by the company Gattefosse; and extracts of *Solanum tuberosum* sold by the company Sederma.

The agents for stimulating keratinocyte differentiation comprise, for example, minerals such as calcium; the extract of lupin sold by the company Silab under the trade name Photopreventine; sodium beta-sitosteryl sulphate sold by the company Seporga under the trade name Phytocohesine; and the extract of corn sold by the company Solabia under the trade name Phytovityl.

Muscle Relaxant.

Besides the sapogenin described above, the composition according to the invention may comprise other muscle relaxants, among which mention may be made in particular of alverine and its salts, especially alverine citrate, manganese gluconate and the hexapeptide argireline R sold by the company Lipotec.

Tensioning Agent.

The term "tensioning agent" means a compound capable of exerting tension on the skin, the effect of which is to temporarily fade out irregularities on the skin's surface, such as wrinkles and fine lines.

Among the tensioning agents that may be used in the composition according to the present invention, mention may be made especially of: (1) synthetic polymers, such as polyurethane latices or acrylic-silicone latices, in particular those described in patent application EP-1 038 519, such as a propylthio(polymethyl acrylate), propylthio(polymethyl methacrylate) and propylthio(polymethacrylic acid) grafted polydimethylsiloxane, or alternatively a propylthio(polyisobutyl methacrylate) and propylthio(polymethacrylic acid) grafted polydimethylsiloxane. Such grafted silicone polymers are sold especially by the company 3M under the trade names VS 80, VS 70 or LO21. (2) polymers of natural origin, especially (a) polyholosides, for example (i) in the form of starch derived especially from rice, corn, potato, cassaya, pea, *Triticum aestivum* wheat, oat, etc. or (ii) in the form of carrageenans, alginates, agars, gelans, cellulose-based polymers and pectins, advantageously as an aqueous dispersion of gel microparticles, and (b) latices consisting of shellac resin, sandarac gum, dammar resins, elemi gums, copal resins and cellulose-based derivatives, and mixtures thereof; (3) plant proteins and protein hydrolysates, in particular from corn, rye, *Triticum aestivum* wheat, buckwheat, sesame, spelt, pea, bean, lentil, soybean and lupin, (3) mixed silicates, especially phyllosilicates and in particular Laponites, (4) wax microparticles chosen, for example, from carnauba wax, candelilla wax and alfalfa wax, (5) colloidal particles of mineral filler with a number-average diameter of between 0.1 and 100 nm and preferably between 3 and 30 nm, chosen, for example, from: silica, cerium oxide, zirconium oxide, alumina, calcium carbonate, barium sulphate, calcium sulphate, zinc oxide and titanium dioxide.

Anti-Pollution Agent or Free-Radical Scavenger.

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

As ozone-trapping agents that may be used in the composition according to the invention, mention may be made in particular of vitamin C and its derivatives including sugar glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulphur-containing amino acid derivatives, in particular S-carboxymethylcysteine; ergothioneine; N-acetylcysteine; chelating agents for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by the Laboratoires Serobiologiques under the trade name CPP LS 2633-12F, the water-soluble fraction of corn sold by the company Solabia under the trade name Phytovityl., the mixture of extract of fumitory and of extract of lemon sold under the name Unicotrozon C-49 by the company Induchem, and the mixture of extracts of ginseng, of apple, of peach, of wheat and of barley, sold by the company Provital under the trade name Pronalen Bioprotect.

As agents for trapping monocyclic or polycyclic aromatic compounds, which may be used in the composition according to the invention, mention may be made in particular of tannins such as ellagic acid; indole derivatives, in particular 3-indolecarbinol; extracts of tea, in particular of green tea, extracts of water hyacinth or *Eichhornia crassipes*; and the water-soluble fraction of corn sold by the company Solabia under the trade name Phytovityl.

Finally, as heavy-metal-trapping agents that may be used in the composition according to the invention, mention may be made in particular of chelating agents such as EDTA, the pentasodium salt of ethylenediaminetetramethylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulphur-containing amino acids such as cysteine; extracts of water hyacinth (*Eichhornia crassipes*); and the water-soluble fraction of corn sold by the company Solabia under the trade name Phytovityl.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin.

Agents Acting on the Capillary Circulation.

The active agents acting on the capillary circulation (vasoprotective or vasodilating agents) are found especially among flavonoids, ruscogenins, esculosides, escin extracted from common horse chestnut, nicotinates, heperidine methyl chalcone, essential oils of lavender or of rosemary, and extracts of *Ammi Visnaga*.

Agents Acting on the Energy Metabolism of Cells.

This expression means active agents acting on the energy metabolism of the skin, such as, for example, and in a non-limiting manner, ATP synthesis, and also those involved in the respiratory chain of the cell or in the energy reserves. Mention may be made in this respect of coenzyme Q10 (ubiquinone), cytochrome C, creatine or phosphocreatine.

As mentioned previously, the composition according to the invention may also contain UVA and/or UVB screening agents, in the form of organic or mineral compounds, the latter optionally being coated to make them hydrophobic.

The organic screening agents may be chosen especially from: anthranilates, in particular menthyl anthranilate; benzophenones, in particular benzophenone-1, benzophenone-3, benzophenone-5, benzophenone-6, benzophenone-8, benzophenone-9, benzophenone-12 and, preferably, benzophenone-2 (oxybenzone) or benzophenone-4 (Uvinul MS40 available from BASF); benzylidenecamphors, in particular 3-benzylidenecamphor, benzylidenecamphorsulphonic acid, camphor benzalkonium methosulphate, polyacrylamidomethylbenzylidenecamphor, terephthalylidenedicamphorsulphonic acid and, preferably, 4-methylbenzylidenecamphor (Eusolex 6300 available from Merck); benzimidazoles, in particular benzimidazilate (Neo Heliopan AP available from Haarmann & Reimer), or phenylbenzimidazolesulphonic acid (Eusolex 232 available from Merck); benzotriazoles, in particular drometrizole trisiloxane, or methylenebisbenzotriazolyltetramethylbutylphenol (Tinosorb M available from Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate and, preferably, ethocrylene (Uvinul N35 available from BASF), octyl methoxycinnamate (Parsol MCX available from Hoffmann LaRoche), or octocrylene (Uvinul 539 available from BASF); dibenzoylmethanes, in particular butylmethoxydibenzoylmethane (Parsol 1789); imidazolines, in particular ethylhexyl dimethoxybenzylidene dioxoimidazoline; PABAs, in particular ethyl dihydroxypropyl PABA, ethylhexyldimethyl PABA, glyceryl PABA, PABA, PEG-25 PABA and, preferably, diethylhexylbutamidotriazone (Uvasorb HEB available from 3V Sigma), ethylhexyltriazone (Uvinul T150 available from BASF) or ethyl PABA (benzocaine); salicylates, in particular dipropylene glycol salicylate, ethylhexyl salicylate, homosalate or TEA salicylate; triazines, in particular anisotriazine (Tinosorb S available from Ciba); drometrizole trisiloxane. The mineral screening agents preferably consist of zinc oxide and/or titanium dioxide, preferably of nanometric size, optionally coated with alumina and/or stearic acid.

Additional antioxidant ingredients and compositions can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood microcirculation improvement ingredients and compositions can be added to compositions that contain Topical treatment agents of the present invention. These are selected from Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), Boswellia Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

The anti-inflammatory ingredients can be added to compositions that contain Topical treatment agents of the present invention. These can be selected from at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and *Emblica* extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), Boswellia Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (Vitis-Vinifera) leaves, apigenin, phytosan, luteolin, and combinations thereof.

Certain divalent metal ions can be added to compositions that contain Topical treatment agents of the present invention. The examples of such metal ions include zinc, copper, manganese, vanadium, chromium, cobalt, and iron.

Determination of the Skin Surface Sebum.

The Measurement Principle. The measurement is based on grease-spot photometry. A special tape becomes transparent in contact with the sebum on the skin surface. For the determination of the sebum, the measuring head of the cassette is inserted into the aperture of the device (SEBUMETER SM 815), where the transparency is measured by a light source sending light through the tape, which is reflected by a little mirror behind the tape. A photocell measures the transparency. The light transmission represents the sebum content on the surface of the measuring area. A microprocessor calculates the result, which is shown on the display in microgram sebum/square cm of the skin.

For testing, 15 panelists were selected. Sample from Example 1 was applied on one cheek, one side of forehead, and one underarm of the panelists. Plain water was applied on the other cheek, the other side of, forehead, and the other underarm of he panelists. After 8 hours Sebumeter evaluated the amount of sebum. The % reduction (or increase) of sebum was calculated from the equation, % Sebum Reduction (or Increase)=$(A)+(B)/(B)\times\%$;

wherein A=amount of sebum where sample of Example 15 was applied, B=amount of sebum where plain water was applied. These data are presented in the Table 1. These data clearly show average sebum reduction of 12.0%, 11.3%, and 6.9% in forehead, cheek, and underarm, respectively. In no panelist an increase of sebum was noted.

TABLE 1

| | % Reduction of Sebum | | |
|---|---|---|---|
| Panelist | Forehead | Cheek | Underarm |
| 1 | 10 | 12 | 6 |
| 2 | 8 | 10 | 4 |
| 3 | 7 | 9 | 6 |
| 4 | 15 | 18 | 8 |
| 5 | 16 | 12 | 5 |
| 6 | 4 | 5 | 2 |
| 7 | 10 | 9 | 4 |
| 8 | 18 | 20 | 12 |
| 9 | 11 | 9 | 7 |
| 10 | 5 | 12 | 10 |
| 11 | 14 | 12 | 11 |
| 12 | 16 | 14 | 9 |
| 13 | 9 | 6 | 4 |
| 14 | 22 | 11 | 9 |
| 15 | 15 | 10 | 6 |
| Average | 12 | 11.3 | 6.9 |

Determination of the Skin Wrinkles Reduction.

The Measurement Principle. The measurement is based on photographic method. The close-up photo of both treated and untreated sites is taken before and after test material application. The sample is applied on crow's feet area of the face near the eyes.

For testing, 15 panelists were selected. Sample from Example 1 was applied on crow's foot near one eye; plain water was applied on the other crow's foot. After 8 hours photographs were taken and evaluated the amount of sebum. The % reduction (or increase) of the depth of wrinkles in each of crow's foot area was evaluated and calculated from the equation, % Wrinkles Reduction (or Increase)=$(A)+(B)/(B)\times\%$;

wherein A=depth of wrinkles where sample of Example 1 was applied, B=depth of wrinkles where plain water was applied. These data are presented in the Table 1. These data clearly show average wrinkles reduction of 63%.

| Panelist | % Reduction Wrinkles Crow's Foot |
|---|---|
| 1 | 78 |
| 2 | 58 |
| 3 | 67 |
| 4 | 55 |
| 5 | 66 |
| 6 | 44 |
| 7 | 60 |
| 8 | 58 |
| 9 | 71 |
| 10 | 65 |
| 11 | 84 |
| 12 | 46 |
| 13 | 59 |
| 14 | 72 |
| 15 | 65 |
| Average | 63 |

EXAMPLES

The following examples are presented to illustrate presently preferred practice thereof. These examples also include the formulation of consumer desirable lotion, cream, and other such compositions for their retail marketing. As illustrations they are not intended to limit the scope of the invention. All quantities are in weight %.

Example 1

Preparation of Diosgenin Gluconate. Ingredients % Weight (1) Deionized water 10.0 (2) Diosgenin 5.0 (3) Polyethylene glycol 81.0 (4) Gluconolactone 4.0. Procedure. Mix (1) to (4) and heat at 80 to 95 degrees Celsius for two hours. A clear solution is obtained, which contains diosgenin gluconate. It can be used directly in subsequent cosmetic preparations.

Tigogenin gluconate and Hecogenin gluconate were similarly prepared by replacing diosgenin by tigogenin and hecogenin, respectively, in the above preparation.

Example 2

Skin Whitening Serum with Sebum Reduction. Ingredients % Weight (1) Deionized water 20.0 (2) Quinacetophenone 5.0 (3) Methylpropanediol 68.0 (4) Dimethicone copolyol 4.0 (5) Preservatives 0.5 (6) Diosgenin gluconate 1.5. (7) Ammonium Acryloyldimethyltaurate/VP copolymer 1.0 Procedure. Make main batch by mixing (2) to (6) at room temperature. Pre-mix (1) and (7) to a clear paste and add to main batch with mixing. The product has a clear to slightly hazy syrup-like light blue appearance, typical of a skin serum product. It is absorbed rapidly with a silky smooth skin feel.

Example 3

Antiaging, Topical Treatment Cream with Hecogenin Gluconate. Ingredients % Weight (1) Deionized water 79.5 (2) Cetearyl alcohol (and) dicetyl phosphate (and) Ceteth-10 phosphate 5.0 (3) Cetyl alcohol 2.0 (4) Glyceryl stearate (and) PEG-100 stearate 4.0 (5) Caprylic/capric triglyceride 5.0 (6) Resacetophenone 3.0 (7) Hecogenin gluconate 1.0 (8) (8) Preservatives 0.5. Procedure. Mix 1 to 5 and heat to 75-80° C. Adjust pH to 4.0 4.5. Cool to 35-40 C with mixing. Add 6 to 8 with mixing. Adjust pH to 4.0-4.5, if necessary. White to off-white cream.

Example 4

Collagen Boosting Sebum Control Facial Mask with Tigogenin Gluconate. Ingredient. % (1) Chitosan 5.0 (2) 2,5-Dihydroxy acetophenone 5.0 (3) Glycerin 17.7 (4) Water 69.8 (5) Tigogenin gluconate 1.5 (6) Zinc Salicylate 0.5 (7). Preservatives 0.5 Procedure: Mix 1,2, and 3 to a paste. Mix 4 to 8 separately to a clear solution. Add this to main batch and mix. A clear gel product is obtained. It is applied on the face and neck and left for 10 to 30 minutes, then rinsed off.

Example 5

Preparation of Ergosterol Gluconate. Ingredients % Weight (1) Deionized water 10.0 (2) Ergosterol 5.0 (3) Polyethylene glycol 81.0 (4) Gluconolactone 4.0. Procedure. Make main batch by mixing (2) to (5) at room temperature. Mix (1) to (4) and heat at 80 to 95 degrees Celsius for two hours. A clear solution is obtained, which contains ergosterol gluconate. It can be used directly in subsequent cosmetic preparations.

Example 6

Age Spot and Sebum Reduction Cream with Ergosterol Gluconate. Ingredient % (1) Water 64.3 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Ergosterol gluconate 1.5 (12) Shea butter 2.0 (13) Tigogenin 1.0 (14) Water 5.0 (15) Zinc Lactate 1.0 (16) Zinc Hydroxycitrate 3.1 (17) 2,4-Dihydroxy Acetophenone (Resacetophenone) 1.1 (18) Paeonol 1.5 (19) Carnosine 0.1 (20) Cyclomethicone, Dimethicone Crosspolymer 2.0 (21) Arbutin 0.5 (22) Polysorbate-20 2.0 (23) Sepigel-305 2.0. Procedure. Mix (1) to (13) and heat at 70 to 80 C till homogenous. Cool to 40 to 50 C. Premix (14) to (16) and add to batch with mixing. Add all other ingredients and mix. Cool to room temperature. An off-white cream is obtained.

Example 7

Acne Cream with Sebum Reduction with a Combination of Diosgenin Gluconate and Ergosterol Gluconate. Ingredient % (1) Water 62.3 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Water 5.0 (15) Diosgenin gluconate and Ergosterol gluconate (1:1 mixture) 4.0 (16) Niacinamide Hydroxycitrate 2.2 (17) 2,4-Dihydroxy Acetophenone (Resacetophenone) 1.1 (18) Hecogenin 1.5 (19) Carnosine 0.1 (20) Cyclomethicone, Dimethicone Crosspolymer 2.0 (21) Arbutin 0.5 (22) Pyridoxine Salicylate (23) Polysorbate-20 2.0 (24) Sepigel-305 2.0. Procedure. Mix (1) to (13) and heat at 70 to 80 C till homogenous. Cool to 40 to 50 C. Premix (14) to (16) and add to batch with mixing. Add all other ingredients and mix. Cool to room temperature. An off-white cream is obtained.

Example 8

Skin Brightening Cleanser with Tigogenin gluconate. Ingredient % (1) PEG-6 63.120 (2) Hydroxypropyl Cellulose 0.3 (3) *Boswellia Serrata* 0.05 (4) Sodium Cocoyl Isethionate 20.0 (5) Sodium Lauryl Sulfoacetate 5.0 (6) L-Glutathione 0.01 (7) Zinc Salicylate 0.11 (8) Protodioscin 0.1 (9) Tigogenin gluconate 0.11 (10) Ascorbic acid 10.0 (11) Phenoxyethanol 0.7 (12) Ethylhexylglycerin 0.3 (13) Fragrance 0.2. Procedure. Mix (1) and (2) to a clear thin gel. Add all other ingredients and mix in a homogenizer. A white cream-like cleanser is obtained.

Example 9

Antiaging Gel with Sebum Reduction with Tigogenin gluconate. Ingredients % (1) Triethyl Citrate 67.75 (2) Ethylenediamine/Hydrogenated Dimer Dilinoleate Copolymer Bis-Di-C14-18 Alkyl Amide 10.0 (3) Ximenia Oil 0.1 (4) Tigogenin gluconate 0.25 (5) Magnolol (and Honokiol 0.2 (6) Protodioscin 0.5 (7) Tetrahydrocurcuminoids 0.2 (8) Zeolite 20.0 (9) Fragrance 1.0. Procedure. Mix (1) and (2) and heat at 80 to 90 C till clear. Cool to 40 to 50 C and add all other ingredients and mix. Cool to room temperature. A white gel-like product is obtained.

Example 10

Anti-Wrinkle Sebum Reduction Transparent Gel with Hecogenin Gluconate and Tigogenin Gluconate. Ingredients % (1) C12-15 Alkyl Benzoate 96.75 (2) Dibutyl Lauroyl Glutamide 1.0 (3) Ximenia Oil 0.1 (4) Tigogenin gluconate 0.25 (5) Magnolol (and Honokiol 0.2 (6) Paeonol 0.5 (7) Tetrahydrocurcuminoids 0.2 (8) Hecogenin gluconate 1.0. Procedure. Mix (1) and (2) and heat at 95 to 110 C till clear. Cool to 40 to 50 C and add all other ingredients and mix. Cool to room temperature. A transparent gel-like product is obtained.

Example 11

Sebum Reduction Spray Lotion with Anti-Inflammatory Agents and Tigogenin Hydroxycitrate. Ingredients % (1) PEG-4 81.0 (2) Triethyl Citrate 16.0 (3) Fragrance 0.5 (4) Paeonol 0.5 (5) Tigogenin Hydroxycitrate 2.0. Procedure. Mix all ingredients till a clear solution is obtained. Fill in spray bottles.

Example 12

Anti-Inflammatory Color-Changing Acne Mask with Sebum Reduction Agents in a Controlled Release Delivery System. Ingredients % (1) Grapeseed oil 34.28 (2) Ethylenediamine/Hydrogenated Dimer Dilinoleate Copolymer Bis-Di-C14-18 Alkyl Amide 5.0 (3) Hecogenin gluconate 2.0 (4) Propyl Paraben 0.3 (5) Jojoba oil 0.5 (6) Sweet Almond oil 4.0 (7) Shea butter 0.2 (8) Mango butter 0.2 (9) Avocado utter 0.2 (10) Murumuru butter 0.2 (11) Color Change Green/Blue dye 0.01 (12) Zinc Hydroxybenzoate 5.5 (13) Vitamin E 0.11 (14) Phenoxyethanol 0.7 (15) Zeolite 31.0 (16) Ethylhexylglycerin 0.5 (17) Laureth-3 15.0 (18) Fragrance 0.5. Procedure. Mix (1) to (10) and heat at 70 to 80 C till clear. Cool to 35 to 45 C and all other ingredients and mix. Cool to room temperature. A light green thin paste is obtained. Upon contact with water, it turns blue and releases heat.

Example 13

Sebum Reduction Shampoo with Protodiosgenin Gluconate. Ingredient % (1) Water 64.2 (2) Protodiosgenin gluconate 1.2 (3) Sodium Lauryl Sulfoacetate 10.0 (4) Disodium Laureth Sulfosuccinate 20.0 (5) Phenoxyethanol 0.7 (6) Chlorphenesin 0.3 (7) PEG-120 Methyl Glucose Dioleate 2.5. (8) Hydrolyzed Soy Protein 0.5 (9) Hydrolyzed Silk Protein 0.5 (10) Oat Extract 0.1. Procedure. Mix (1) to (7) and heat at 60 to 70 C to a clear solution. Cool to 35 to 40 C and add all other ingredients and mix. Cool to room temperature.

Example 14

Scalp Sebum Reduction Lotion with Protodiosgenin Gluconate. Ingredients % (1) Water 39.158 (2) Acrylates/C10-30 Alkyl Acrylate Crosspolymer 0.5 (3) Escin 0.1 (4) Sodium Stearyl Phthalamate 1.0 (5) Sodium Hydroxide 0.142 (6) Cetyl Alcohol 4.0 (7) Phenoxyethanol 0.7 (8) Chlorphenesin 0.3 (9) Triethyl Citrate 10.0 (10) Ethylhexylglycein 0.5 (11) Protodiosgenin gluconate 10.0 (12) PEG-6 2.0 (13) Tetrahydrocurcuminoids 0.1 (14) Magnolol 0.1 (15) Paeonol 0.2 (16) Fragrance 1.0. Procedure. Mix (1) to (11) and heat at 80 to 90 C till clear. Cool to 45 to 55. Pre-mix (12) to (16) and add to main batch and mix. Cool to room temperature and adjust pH to 7.5.

Example 15

Sebum Reduction Make-up Remover Fluid with Hecogenin Gluconate. Ingredients % (1) Water 39.158 (2) Acrylates/C10-30 Alkyl Acrylate Crosspolymer 0.5 (3) Hecogenin gluconate 0.1 (4) Sodium Stearyl Phthalamate 1.0 (5) Sodium Hydroxide 0.142 (6) Cetyl Alcohol 4.0 (7) Phenoxyethanol 0.7 (8) 1,2-Octanediol 0.3 (9) Triethyl Citrate 10.0 (10) Methyl Soyate 30.0 (11) Ethylhexylglycein 0.5 (12) Polysorbate-20 10.0 (13) PEG-6 2.0 (14) Tetrahydrocurcuminoids 0.1 (15) Magnolol 0.1 (16) Dioscin 0.2 (17) Fragrance 1.0. Procedure. Mix (1) to (12) and heat at 80 to 90 C till clear. Cool to 45 to 55. Pre-mix (13) to (16) and add to main batch and mix. Add (17) and mix. Cool to room temperature and adjust pH to 7.5.

Example 16

Test Solution of Diosgenin gluconate. Ingredients % (1) Polyethylene glycol qs (2) Diosgenin gluconate solution 2% active content (from Example 1). Mix two ingredients at 40 to 50 C to a clear solution.

Example 17

Preparation of Garcinol Gluconate. Ingredients % Weight (1) Deionized water 10.0 (2) Garcinol 5.0 (3) Polyethylene glycol 81.0 (4) Gluconolactone 4.0. Procedure. Mix (1) to (4) and heat at 80 to 95 degrees Celsius for two hours. A clear solution is obtained, which contains garcinol gluconate. It can be used directly in subsequent cosmetic preparations.

Example 17

Preparation of Garcinol Gluconate. Ingredients % Weight (1) Deionized water 10.0 (2) Garcinol 5.0 (3) Polyethylene glycol 81.0 (4) Gluconolactone 4.0. Procedure. Mix (1) to (4)

and heat at 80 to 95 degrees Celsius for two hours. A clear solution is obtained, which contains garcinol gluconate. It can be used directly in subsequent cosmetic preparations.

Example 18

Alternate Preparation of Garcinol Gluconate. Ingredients % Weight (1) Polyethylene glycol 10.0 (2) Garcinol 5.0 (3) Triethyl citrate 81.0 (4) Gluconolactone 4.0. Procedure. Mix (1) to (4) and heat at 80 to 95 degrees Celsius for two hours. A clear solution is obtained, which contains garcinol gluconate. It can be used directly in subsequent cosmetic preparations.

Example 19

Preparation of Forskohlin Gluconate. Ingredients % Weight (1) Deionized water 10.0 (2) Forskohlin 5.0 (3) Polyethylene glycol 81.0 (4) Gluconolactone 4.0. Procedure. Mix (1) to (4) and heat at 80 to 95 degrees Celsius for two hours. A clear solution is obtained, which contains forskohlin gluconate. It can be used directly in subsequent cosmetic preparations.

Example 20

Preparation of Forskohlin Glucuronate. Ingredients % Weight (1) Deionized water 10.0 (2) Forskohlin 5.0 (3) Polyethylene glycol 81.0 (4) Glucuronolactone 4.0. Procedure. Mix (1) to (4) and heat at 80 to 95 degrees Celsius for two hours. A clear solution is obtained, which contains forskohlin glucuronate. It can be used directly in subsequent cosmetic preparations.

Example 21

Preparation of Diosgenin Glucuronate. Ingredients % Weight (1) Deionized water 10.0 (2) Diosgenin 5.0 (3) Polyethylene glycol 81.0 (4) Glucuronolactone 4.0. Procedure. Mix (1) to (4) and heat at 80 to 95 degrees Celsius for two hours. A clear solution is obtained, which contains diosgenin glucuronate. It can be used directly in subsequent cosmetic preparations.

Clinical Testing for the Treatment of Skin Condition.
Clinical Testing I: Serum A Versus Placebo.

The sample from Example 1 was coded as Serum A. Placebo was a sample made according to Example 1 in which diosgenin was not included, and it was replaced by polyethylene glycol.

Ballistometry showed a decrease in skin stiffness at 1 week in the treated group, and an increase in the placebo group. The placebo group continues to increase in stiffness at one month. This study started in the late summer and as the season changes the temperature has dropped considerably and the humidity is lower. Typically we start to see the onset of drier skin as colder weather progresses. The amplitude measurement has a decrease in the placebo group, but the treated group had a slight increase. As skin ages, we generally see a decrease in the amplitude measurement.

Laser Doppler: There was an increase in the microcirculation of the skin at the 1-week measurement in both the placebo and treated groups. There was no change at the 1-month measurement. Silastic Castings: These results are reported as % change in fine lines and wrinkles. The castings at 1 week and 1 month were compared to the baseline castings. The castings obtained from the treated group showed a greater decrease in fine lines and wrinkles.

| | | Fine Lines & Wrinkles | | |
|---|---|---|---|---|
| | | Increase | No Change | Decrease |
| PLACEBO | 1 Week | 63 | 30 | 7 |
| | 1 Month | 70 | 23 | 7 |
| TREATED | 1 Week | 30 | 30 | 40 |
| | 1 Month | 25 | 25 | 50 |

Photographic Assessment at 1 Month: Photographs were evaluated for skin texture, pigmentation, pore-size, skin tone and clarity. Treated-8 of 15 subjects showed an overall improvement in their skin. Placebo-2 of 15 subjects showed an overall improvement in their skin.

Conclusions of Clinical Testing (I).
1. Comparison of the Treated Group Versus the Placebo Group Exhibited:
Reduced breakouts.
Softer skin; smoother complexion.
Skin looks and feels brighter and fresh.
Reduced pore-size; less facial oil.
2. Subject's Assessment of their Skin:

The subjects were asked to evaluate the skin care regimen that they were prescribed.
Placebo—6 of 15 report a positive response to the prescribed skin care.
Treated—14 out of 15 report a positive response to the prescribed skin care.
3. Safety/Adverse Reactions:
There were no reported incidences of skin irritation during this study.
Clinical Testing II: Serum A versus Serum B versus Placebo.

The study was a double blinded, pilot, controlled, single center study. A total of 24 subjects participated in the study. They were divided into two groups of 12 subjects each. The test samples (with and without diosgenin gluconate) were made as described in Example 2. Group-A, applied the Serum-A (sample from Example 1), while the Group-B applied the Serum-B (sample from Example 2). Each subject was asked to use the given test products on left under-eye for a period of 4 weeks. The right under-eye was the untreated eye. The subjects were assessed on 0 day, and at the end of the $1^{st}$, $2^{nd}$, $3^{rd}$ and the $4^{th}$ week. The assessment was carried out by a Dermatologist for the improvement in the (1) dark circles, (2) puffiness, and (3) wrinkles under the eye. Elastometer readings were taken for the crowfeet area to assess the improvement in skin elasticity.

2.1 Investigational Products.
The investigational products were the two under eye serum formulations and were coded A and B as follows:
Serum from Example 2: Serum-A (With diosgenin gluconate).
Serum Modified from Example 2: Serum-B (Only ascorbic acid, no diosgenin gluconate).
2.2 Controls for the Study.
The right under-eye was untreated and that was taken as the control untreated site.
2.3 Subject Population.
Total 24 subjects were selected as per the inclusion and exclusion criteria.
2.4 Inclusion Criteria:
i. Male and Female (30:70) subjects in generally good health.

ii. Subjects in the age group of 25-45 years.
iii. Subject has not participated in a similar investigation in the past four weeks.
iv. Subjects have not used similar products for the last 4 weeks.
v. Subjects willing to give a written informed consent and come for regular.
vi. Follow-up.
vii. Subjects should have an under eye puffiness score of 2-3, and under eye dark circle score of 2-3 as mentioned in section 9 of this protocol.

2.5 Exclusion Criteria
i. A Known history or present condition of Allergic response to any cosmetic product.
ii. Subject having skin disease (e.g. psoriasis, atomic dermatitis or other cutaneous manifestations), which would interfere with the test readings.
iii. Subjects having melasma.
iv. Subjects on medications (e.g. steroids or antihistamines), which would compromise the study.
v. The subject is pregnant/nursing.

2.6 Duration of Study: Four Weeks.
3.0 Study Outline.
3.1 Product Application.

The respective test sample was provided to the subjects after the baseline reading. The subjects applied approximately 0.5 grams of the test products on the left under-eye and evenly spread the product gently extending up to the crowfeet region with light strokes till absorbed into the skin. The right under-eye was considered as control or untreated site. The test sample was applied twice daily (i.e. once after bath and second before bedtime) for a period of four weeks on the left under eye region.

3.2 Clinical Measurements.
3.2.1 Visual Assessment of Under-Eye (By Dermatologist).

The dermatologist graded the both the under-eyes of the subjects on the baseline day and at the end of the $1^{st}$, $2^{nd}$, $3^{rd}$ and $4^{th}$ week as per the following criteria.

(1) Dark circles—The dermatologist graded the under eye dark circles on both the left and right under-eye by using the following scale (half points used when necessary):

| Description | Score |
| --- | --- |
| No dark circles | 0 |
| Mild dark circles | 1 |
| Moderate dark circles | 2 |
| Severe dark circles | 3 |

(2) Puffiness—The dermatologist graded the under eye puffiness on both the left and right under-eye by using the following scale (half points used when necessary):

| Description | Score |
| --- | --- |
| No puffiness | 0 |
| Mild puffiness | 1 |
| Moderate puffiness | 2 |
| Severe puffiness | 3 |

(3) Wrinkles—The dermatologist graded the under eye wrinkles on both the left and right under-eye by using the following scale (half points used when necessary):

| Description | Score |
| --- | --- |
| No wrinkles | 0 |
| Very fine lines | 1 |
| Moderate wrinkles | 2 |
| Deep set wrinkles | 3 |

3.2.3 Instrumental Assessment.
Elastometer: Skin elasticity of both the crowfeet area was recorded using Elastometer.

4.0 Results and Statistical Analysis.
4.1 Dermatologist's Assessment.
4.1.1 Dark Circles.

Serum-A. Compared to the baseline scores, there is a good improvement in the dark circle scores for the treated under-eye. The scores for the untreated under-eye also seem to improve albeit only to a small extent. Serum-B. Compared to the baseline scores, there is a good improvement in the dark circle scores for the treated under-eye. The scores for the untreated under-eye also seem to improve albeit only to a small extent. However, the differences in improvement between untreated & treated under-eye scores are not statistically significant. 5 of the 12 subjects in the Serum-B group showed significant improvement in the reduction of dark circles.

Serum-A Compared to Serum-B. If the improvements in the scores for the treated under-eye over the improvements in the scores for the untreated under-eye are compared, there is no statistically significant difference between the improvement in dark circles due to Serum-A and Serum-B, although the stability of Serum A is better.

4.1.2 Puffiness.
Serum-A. Compared to the baseline scores, there is a good improvement in the puffiness scores for the treated under-eye. The scores for the untreated under-eye also seem to improve albeit only to a small extent.

Serum-B. Compared to the baseline scores, there is a good improvement in the puffiness scores for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, there is no statistically significant difference between the improvement in puffiness due to Serum-A and Serum-B, although the stability of Serum A is better.

4.1.3 Wrinkles.
Serum-A. Compared to the baseline scores, there is a good improvement in the scores for wrinkles for the treated under-eye. The scores for the untreated under-eye also seem to improve albeit only to a small extent.

Serum-B. Compared to the baseline scores, there is a good improvement in the scores for wrinkles for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, Serum-A shows better improvement in reduction of wrinkles post week-3, and the stability of Serum A is better.

4.2 Instrumental Assessment of Crowfeet Area: Elastometer.

Serum-A. Compared to the baseline scores, there is an improvement in the Elastometer readings scores for the treated crowfeet area. Eight of the 11 subjects show significant improvement in Elastometer readings for the treated crowfeet area.

Serum-B. Compared to the baseline scores, there is an improvement in the Elastometer readings scores for the treated crowfeet area. However, the extent of improvement is fluctuating over the four-week period.

Serum-A Compared to Serum-B. There is no statistically significant difference between Serum-A and Serum-B, although serum A is directionally better, and the stability of Serum A is also better.

Conclusion of Clinical Testing.

Based on the data it is generally seen that for all the under-eye attributes (dark circle, puffiness, and wrinkles), good amount of improvement is seen after week-3 for Serum-A (Diosgenin gluconate), compared to untreated area.

The invention claimed is:

1. A sugar ester of a polycyclic polyisoprenoid of formula (I);

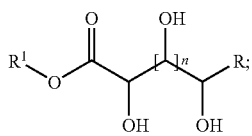
(I)

Wherein, n = 0, 1, 2, and 3; and

R = H, —CH$_2$OH, —CH(OH)—CH$_2$OH, and —CH(OH)—CH(OH)—CH$_2$OH; and

R$^1$ = a polycyclic polyisoprenoid substituent selected from the group consisting of:

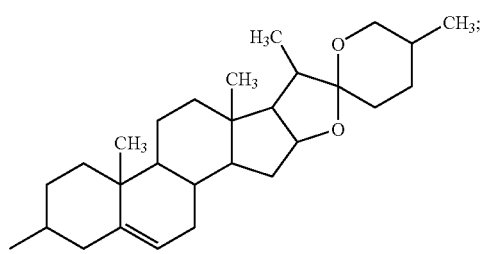
(II)

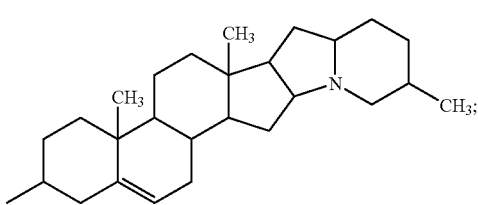
(III)

-continued

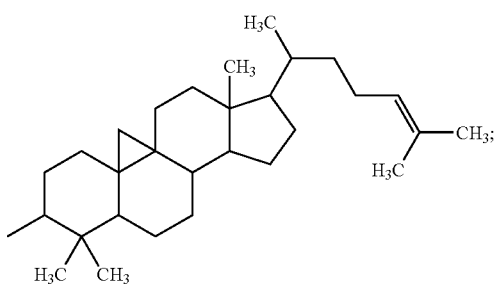
(IV)

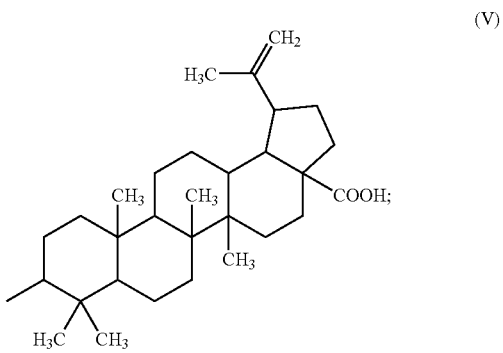
(V)

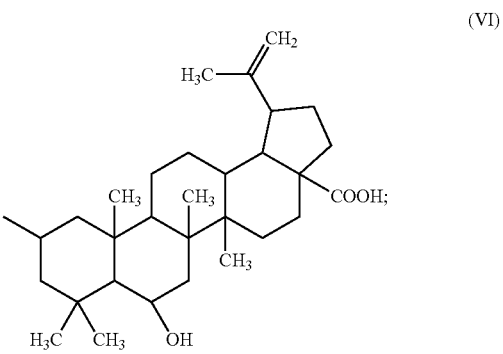
(VI)

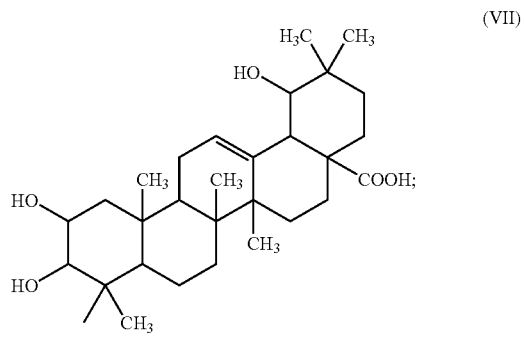
(VII)

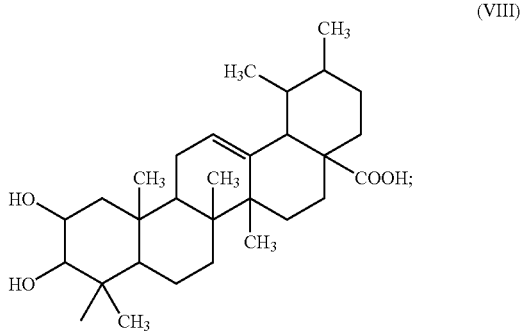
(VIII)

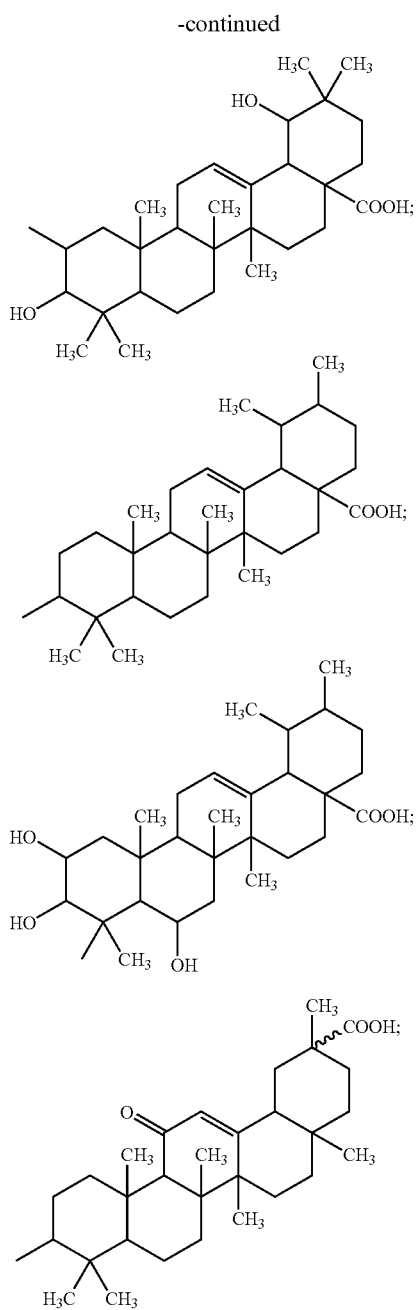
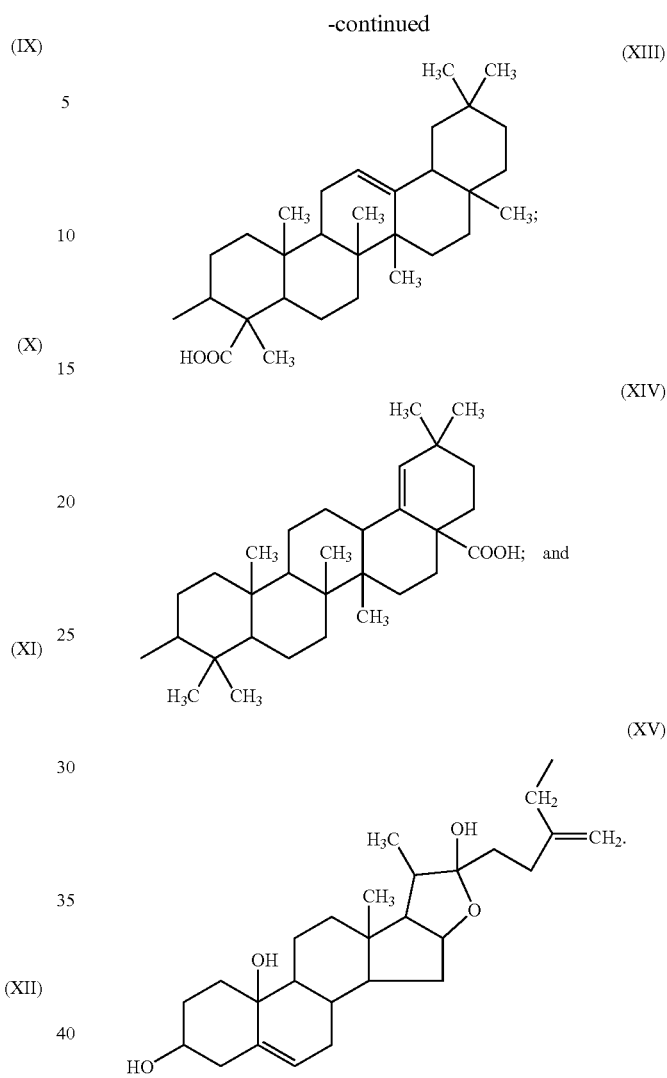
2. A compound of claim 1, wherein said compound is selected from its various optically active, which is d or l; optically inactive; optically racemic, which is dl or meso; cis or trans; and geometric isomers.
3. A composition comprising the compound of claim 1, wherein said compound is Diosgenin gluconate of formula (XVI),
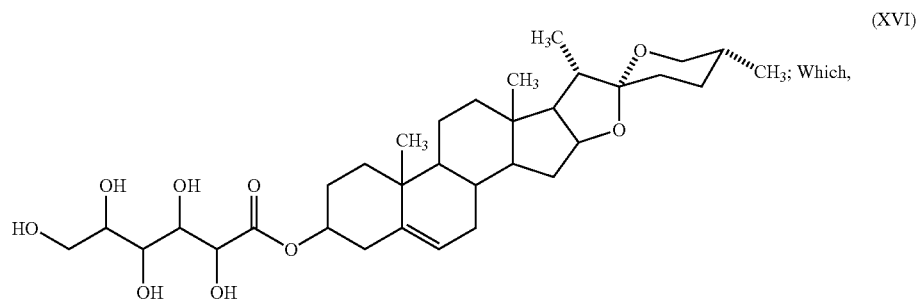
In formula (I): n=3, R=H, and R$^1$=(II)

4. A compositions comprising the compound of claim 1 for the treatment of a dermatological disorder selected from the group consisting of age spots, acne, collagen loss, loss of skin pliability, loss of skin suppleness, skin wrinkles and fine lines, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, nail or skin requiring cleansers, conditioning or treatment, and hair or scalp requiring shampooing or conditioning, and combinations thereof.

5. A composition comprising the compound of claim 1, wherein said compound is further selected from the group consisting of diosgenin gluconate, diosgenin galactonate, diosgenin mannonate, diosgenin arabinate, glucooctanate, diosgenin erythronate, diosgenin glyceromannoheptonate, diosgenin galactoheptonate, tigogenin gluconate, tigogenin galactonate, tigogenin mannonate, tigogenin arabinate, tigogenin glucooctanate, tigogenin erythronate, tigogenin glyceromannoheptonate, tigogenin galactoheptonate, divergioic acid gluconate, divergioic acid galactonate, divergioic acid mannonate, divergioic acid arabinate, divergioic acid glucooctanate, divergioic acid errythronate, divergioic acid glyceromannoheptonate, divergioic acid galactoheptonate, sericic acid gluconate, sericic acid galactonate, sericic acid mannonate, sericic acid arabinate, sericic acid glucooctanate, sericic acid errythronate, sericic acid glyceromannoheptonate, sericic acid galactoheptonate, asiatic acid gluconate, asiatic acid galactonate, asiatic acid mannonate, asiatic acid arabinate, asiatic acid glucooctanate, asiatic acid errythronate, asiatic acid glyceromannoheptonate, asiatic acid galactoheptonate, tormetic acid gluconate, tormetic acid galactonate, tormetic acid mannonate, tormetic acid arabinate, tormetic acid glucooctanate, tormetic acid errythronate, tormetic acid glyceromannoheptonate, tormetic acid galactoheptonate, ursolic acid gluconate, ursolic acid galactonate, ursolic acid mannonate, ursolic acid arabinate, ursolic acid glucooctanate, ursolic acid errythronate, ursolic acid glyceromannoheptonate, ursolic acid galactoheptonate, madecassic acid gluconate, madecassic acid galactonate, madecassic acid mannonate, madecassic acid arabinate, madecassic acid glucooctanate, madecassic acid errythronate, madecassic acid glyceromannoheptonate, madecassic acid galactoheptonate, glycyrrhizic acid gluconate, glycyrrhizic acid galactonate, glycyrrhizic acid mannonate, glycyrrhizic acid arabinate, glycyrrhizic acid glucooctanate, glycyrrhizic acid errythronate, glycyrrhizic acid glyceromannoheptonate, glycyrrhizic acid galactoheptonate, glycyrrhetinic acid gluconate, glycyrrhetinic acid galactonate, glycyrrhetinic acid mannonate, glycyrrhetinic acid arabinate, glycyrrhetinic acid glucooctanate, glycyrrhetinic acid errythronate, glycyrrhetinic acid glyceromannoheptonate, glycyrrhetinic acid galactoheptonate, boswellic acid gluconate, boswellic acid galactonate, boswellic acid mannonate, boswellic acid arabinate, boswellic acid glucooctanate, boswellic acid errythronate, boswellic acid glyceromannoheptonate, boswellic acid galactoheptonate, moronic acid gluconate, moronic acid galactonate, moronic acid mannonate, moronic acid arabinate, moronic acid glucooctanate, moronic acid errythronate, moronic acid glycerornannoheptonate, moronic acid galactoheptonate, ruscogenin gluconate, ruscogenin galactonate, ruscogenin mannonate, ruscogenin arabinate, ruscogenin glucooctanate, ruscogenin errythronate, ruscogenin glycerornannoheptonate, ruscogenin galactoheptonate, and combinations thereof.

6. A composition comprising the compound of claim 1, and a carrier or base.

7. A composition comprising the compound of claim 1 for topical application.

8. A composition according to claim 5, wherein said compound is diosgenin gluconate.

9. A composition according to claim 4, wherein said topical condition is acne.

10. A composition according to claim 4, wherein said topical condition is skin wrinkles including fine lines.

11. A method of treatment of skin condition selected from the group consisting of age spots, acne, collagen loss, loss of skin pliability, loss of skin suppleness, skin wrinkles and fine lines, damage from UV, dry skin, xerosis, ichthyosis, dandruff, brownish spots, keratoses, melasma, lenticiines, liver spots, pgimented spots, dark circles under the eyes, skin pigmentation including darkened skin, blemishes, oily skin, warts, eczema, pruritic skin, psoriasis, inflammatory dermatoses, topical inflammation, nail or skin requiring cleansers, conditioning or treatment, and hair or scalp requiring shampooing or conditioning, and combinations thereof in a subject comprising administering the compound of claim 1 to the subject; and wherein,
   (i) Said compound having been applied topically at a desired site in a sufficient quantity, and, wherein
   (ii) Said application having been done either by a manual or a mechanical method, or a combination thereof; and, wherein
   (iii) Said application is repeated as necessary, and, wherein
   (iv) Said application causes the desired treatment of said skin condition.

12. A method according to claim 11, wherein said skin condition is skin wrinkles including fine lines.

13. A process for making a compound of claim 1, which comprises combining;
   (i) A polyhydroxy lactone, and,
   (ii) A polycyclic polyisoprenoid with a free hydroxyl group, and
   (iii) A liquid reaction medium, and
   (iv) Heating at 50 to 120 degrees Celsius.

14. A process according to claim 13, wherein said polyhydroxy lactone is gluconolactone.

15. A process according to claim 13, wherein said polycyclic polyisoprenoid is diosgenin.

16. A process according to claim 13, wherein said liquid reaction medium is selected from the group consisting of water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methyl pyrrolidone, pyrrolidone, triethyl citrate, and combinations thereof.

17. A process according to claim 16, wherein said liquid reaction medium is polyethylene glycol.

* * * * *